(12) United States Patent
Grueneberg et al.

(10) Patent No.: US 7,612,195 B2
(45) Date of Patent: Nov. 3, 2009

(54) RETROVIRAL VECTORS FOR DELIVERY OF INTERFERING RNA

(75) Inventors: Dorre Grueneberg, Newtonville, MA (US); Gerard Bain, Shrewsbury, MA (US); Nayantara Kothari, Waltham, MA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 12 days.

(21) Appl. No.: 10/574,416

(22) PCT Filed: Oct. 21, 2004

(86) PCT No.: PCT/US2004/034932
§ 371 (c)(1),
(2), (4) Date: Mar. 31, 2006

(87) PCT Pub. No.: WO2005/042754
PCT Pub. Date: May 12, 2005

(65) Prior Publication Data
US 2006/0252153 A1  Nov. 9, 2006

Related U.S. Application Data

(60) Provisional application No. 60/513,313, filed on Oct. 22, 2003, now abandoned.

(51) Int. Cl.
*C07H 21/04* (2006.01)
(52) U.S. Cl. .................. 536/24.5; 536/24.31; 436/6; 436/325; 436/375; 514/44
(58) Field of Classification Search ............... None
See application file for complete search history.

(56) References Cited

U.S. PATENT DOCUMENTS 5,624,803 A * 4/1997 Noonberg et al. ............... 435/6

2004/0234504 A1 * 11/2004 Verma et al. ............... 424/93.2

FOREIGN PATENT DOCUMENTS

WO  WO 2004/022722  3/2004

OTHER PUBLICATIONS

Devroe et al. Retrovirus-delivered siRNA, BMC Biotechnology 2002, vol. 2: 1-5.*
Barton et al. Retroviral delivery of small interfering RNA into prmary cells. PNAS 2002, vol. 99: No. 23: 14943-14945.*
Chang et al. The molecular genetics of Lentiviral vectors—Current and Future Perspectives. Current Gene Therapy 2001, vol. 1: 237-251.*
Devroe et al., Retrovirus-delivered siRNA, BMC Technology, Biomed Central, Aug. 28, 2002, pp. 1-5.
Lieberman et al., Interfering with disease: opportunities and roadblocks to harnessing RNA interference, Trends in Molecular Medicine, Sep. 2003, vol. 9, No. 9, pp. 397-403.
Liu et al, Short hairpin RNA and retroviral vector-mediated silencing of p53 in mammalian cells, Biochem. & Biophys. Res. Comm., Oct. 12, 2004, vol. 324, No. 4, pp. 1173-1178.
Mitta et al., Advanced modular self-inactivating lentiviral expression vectors for multigene interventions in mammalian cells and in vivo transuction, Nucleic Acids Research, Nov. 1, 2002, vol. 30, No. 21, pp. E113.1 to E113.18.
Tiscornia et al., A general method for gene knockdown in mice by using lentiviral vectors expressing small interfering RNA, PNAS, vol. 100, No. 4, Feb. 18, 2004, pp. 1844-1848.
Rubinson et al., A lentivirus-based system to functionally silence genes in primary mammalian cells, stem cells and transgenic mice by RNA interference, Nature Genetics, vol. 33, No. 3, Mar. 2003, pp. 401-406.

* cited by examiner

*Primary Examiner*—Kimberly Chong

(57) ABSTRACT

Provided herein are retroviral vectors for delivering interfering RNA into cells.

10 Claims, 12 Drawing Sheets

FIGURE 1 pLenti-U6-Blasti
aatgtagtcttatgcaatactcttgtagtcttgcaacatggtaacgatgagttagcaacatgccttacaaggagagaaaaagcaccgtgcatgccgatt
ggtggaagtaaggtggtacgatcgtgccttattaggaaggcaacagacgggtctgacatggattggacgaaccactgaattgccgcattgcagagat
attgtatttaagtgcctagctcgatacataaacgggtctctctggttagaccagatctgagcctgggagctctctggctaactagggaacccactgctta
agcctcaataaagcttgccttgagtgcttcaagtagtgtgtgcccgtctgttgtgtgactctggtaactagagatccctcagacccttttagtcagtgtgg
aaaatctctagcagtggcgcccgaacagggacttgaaagcgaaagggaaaccagaggagctctctcgacgcaggactcggcttgctgaagcgcg
cacggcaagaggcgaggggcggcgactggtgagtacgccaaaaattttgactagcggaggctagaaggagagagatgggtgcgagagcgtcag
tattaagcgggggagaattagatcgcgatgggaaaaaattcggttaaggccagggggaaagaaaaaatataaattaaaacatatagtatgggcaag
cagggagctagaacgattcgcgagttaatcctggcctgttagaaacatcagaaggctgtagacaaatactgggacagctacaaccatccttcagaca
ggatcagaagaacttagatcattatataatacagtagcaaccctctattgtgtgcatcaaaggatagagataaaagacaccaaggaagctttagacaa
gatagaggaagagcaaaacaaaagtaagaccaccgcacagcaagcggccgctgatcttcagacctggaggaggagatatgagggacaattgga
gaagtgaattatataaatataaagtagtaaaaattgaaccattaggagtagcacccaccaaggcaaagagaagagtggtgcagagagaaaaaagag
cagtgggaataggagctttgttccttgggttcttgggagcagcaggaagcactatgggcgcagcgtcaatgacgctgacggtacaggccagacaat
tattgtctggtatagtgcagcagcagaacaatttgctgagggctattgaggcgcaacagcatctgttgcaactcacagtctggggcatcaagcagctc
caggcaagaatcctggctgtggaaagatacctaaaggatcaacagctcctggggatttggggttgctctggaaaactcatttgcaccactgctgtgcc
ttggaatgctagttggagtaataaatctctggaacagatttggaatcacacgacctggatggagtgggacagagaaattaacaattacacaagcttaat
acactccttaattgaagaatcgcaaaaccagcaagaaaagaatgaacaagaattattggaattagataaatgggcaagtttgtggaattggtttaacat
aacaaattggctgtggtatataaaattattcataatgatagtaggaggcttggtaggtttaagaatagttttgctgtactttctatagtgaatagagttagg
cagggatattcaccattatcgtttcagacccacctcccaaccccgaggggacccgacaggcccgaaggaatagaagaagaaggtggagagagag
acagagacagatccattcgattagtgaacggatctcgacggtaatcgattttcccatgattccttcatatttgcatatacgatacaaggctgttagagaga
taattagaattaatttgactgtaaacacaaagatattagtacaaaatacgtgacgtagaaagtaataatttcttgggtagtttgcagtttttaaaattatgtttt
aaaatggactatcatatgcttaccgtaacttgaaagtatttcgatttcttggctttatatatcttgtggaaaggacgaaacaccgaattcaccggtcggtta
gtaatgagtttggaattaattctgtggaatgtgtgtcagttaggggtgtggaaagtccccaggctccccaggcaggcagaagtatgcaaagcatgcatct
caattagtcagcaaccaggtgtggaaagtccccaggctccccagcaggcagaagtatgcaaagcatgcatctcaattagtcagcaaccatagtccc
gcccctaactccgcccatcccgcccctaactccgcccagttccgcccattctccgccccatggctgactaatttttttatttatgcagaggccgaggc
cgcctctgcctctgagctattccagaagtagtgaggaggcttttttggaggcctaggcttttgcaaaaagctcccgggagcttgtatatccattttcggat
ctgatcagcacgtgttgacaattaatcatcggcatagtatatcggcatagtataatacgacaaggtgaggaactaaaccatggccaagcctttgtctca
agaagaatccaccctcattgaaagagcaacggctacaatcaacagcatcccccatctctgaagactacagcgtcgccagcgcagctctctctagcga
cggccgcatcttcactggtgtcaatgtatatcatttactgggggaccttgtgcagaactcgtggtgctgggcactgctgctgctgcggcagctggcaa
cctgacttgtatcgtcgcgatcggaaatgagaacaggggcatcttgagccctgcggacggtgccgacaggtgcttctcgatctgcatcctgggatc
aaagccatagtgaaggacagtgatggacagccgacgcagttgggattcgtgaattgctgccctctggttatgtgtggagggctaagcacaattcg
agctcggtacctttaagaccaatgacttacaaggcagctgtagatcttagccacttttaaaagaaaagggggactggaagggctaattcactccca
acgaagacaagatctgcttttgcttgtactgggtctctctggttagaccagatctgagcctgggagctctctggctaactagggaacccactgcttaag
cctcaataaagcttgccttgagtgcttcaagtagtgtgtgcccgtctgttgtgtgactctggtaactagagatccctcagacccttttagtcagtgtggaa
aatctctagcagtagtagttcatgtcatcttattattcagtatttataacttgcaaagaaatgaatatcagagagtgagaggaacttgtttattgcagcttata
atggttacaaataaagcaatagcatcacaaatttcacaaataaagcatttttttcactgcattctagttgtggtttgtccaaactcatcaatgtatcttatcat
gtctggctctagctatcccgcccctaactccgcccatcccgcccctaactccgcccagttccgcccattctccgccccatggctgactaatttttttattt
atgcagaggccgaggccgcctcggcctctgagctattccagaagtagtgaggaggcttttttggaggcctagggacgtacccaattcgccctatagt
gagtcgtattacgcgcgctcactggccgtcgttttacaacgtcgtgactgggaaaaccctggcgttacccaacttaatcgccttgcagcacatccccct
ttcgccagctggcgtaatagcgaagaggcccgcaccgatcgcccttcccaacagttgcgcagcctgaatggcgaatgggacgcgccctgtagcgg
cgcattaagcgcggcgggtgtggtggttacgcgcagcgtgaccgctacacttgccagcgccctagcgcccgctcctttcgctttcttcccttcctttct
cgccacgttcgccggctttccccgtcaagctctaaatcggggggctccctttagggttccgatttagtgctttacggcacctcgaccccaaaaaacttga
ttagggtgatggttcacgtagtgggccatcgccctgatagacggtttttcgccctttgacgttggagtccacgttctttaatagtggactcttgttccaaac
tggaacaacactcaacccctatctcggtctattcttttgatttataagggattttgccgatttcggcctattggttaaaaaatgagctgatttaacaaaaattta
acgcgaattttaacaaaatattaacgcttacaatttaggtggcacttttcggggaaatgtgcgcggaacccctatttgt

FIGURE 1 (CONT.)

```
 5   ttatttttctaaatacattcaaatatgtatccgctcatgagacaataaccctgataaatgcttcaataatattgaaaaaggaagagtatgagtattcaacattt
     ccgtgtcgcccttattccctttttgcggcattttgccttcctgttttgctcacccagaaacgctggtgaaagtaaaagatgctgaagatcagttgggtgc
     acgagtgggttacatcgaactggatctcaacagcggtaagatccttgagagttttcgccccgaagaacgttttccaatgatgagcacttttaaagttctg
     ctatgtggcgcggtattatcccgtattgacgccgggcaagagcaactcggtcgccgcatacactattctcagaatgacttggttgagtactcaccagtc
     acagaaaagcatcttacggatggcatgacagtaagagaattatgcagtgctgccataaccatgagtgataacactgcggccaacttacttctgacaac
10   gatcggaggaccgaaggagctaaccgcttttttgcacaacatgggggatcatgtaactcgccttgatcgttgggaaccggagctgaatgaagccata
     ccaaacgacgagcgtgacaccacgatgcctgtagcaatggcaacaacgttgcgcaaactattaactggcgaactacttactctagcttcccggcaac
     aattaatagactggatggaggcggataaagttgcaggaccacttctgcgctcggcccttccggctggctggtttattgctgataaatctggagccggt
     gagcgtgggtctcgcggtatcattgcagcactggggccagatggtaagccctcccgtatcgtagttatctacacgacggggagtcaggcaactatgg
     atgaacgaaatagacagatcgctgagataggtgcctcactgattaagcattggtaactgtcagaccaagtttactcatatatactttagattgatttaaaa
15   cttcattttaatttaaaaggatctaggtgaagatccttttttgataatctcatgaccaaaatcccttaacgtgagttttcgttccactgagcgtcagaccccgt
     agaaaagatcaaaggatcttcttgagatcctttttttctgcgcgtaatctgctgcttgcaaacaaaaaaaccaccgctaccagcggtggtttgtttgccg
     gatcaagagctaccaactctttttccgaaggtaactggcttcagcagagcgcagataccaaatactgttcttctagtgtagccgtagttaggccaccac
     ttcaagaactctgtagcaccgcctacatacctcgctctgctaatcctgttaccagtggctgctgccagtggcgataagtcgtgtcttaccgggttggact
     caagacgatagttaccggataaggcgcagcggtcgggctgaacggggggttcgtgcacacagcccagcttggagcgaacgacctacaccgaact
20   gagatacctacagcgtgagctatgagaaagcgccacgcttcccgaagggagaaaggcggacaggtatccggtaagcggcagggtcggaacagg
     agagcgcacgagggagcttccaggggggaaacgcctggtatctttatagtcctgtcgggtttcgccacctctgacttgagcgtcgatttttgtgatgctc
     gtcaggggggcggagcctatggaaaaacgccagcaacgcggcctttttacggttcctggccttttgctggccttttgctcacatgttctttcctgcgttat
     cccctgattctgtggataaccgtattaccgcctttgagtgagctgataccgctcgccgcagccgaacgaccgagcgcagcgagtcagtgagcgagg
     aagcggaagagcgcccaatacgcaaaccgcctctccccgcgcgttggccgattcattaatgcagctggcacgacaggtttcccgactggaaagcg
25   ggcagtgagcgcaacgcaattaatgtgagttagctcactcattaggcaccccaggctttacactttatgcttccggctcgtatgttgtgtggaattgtga
     gcggataacaatttcacacaggaaacagctatgaccatgattacgccaagcgcgcaattaaccctcactaaagggaacaaaagctggagctgcaa
     gctt
```

FIGURE 2

5   pLenti-U6-hrGFP
    aatgtagtcttatgcaatactcttgtagtcttgcaacatggtaacgatgagttagcaacatgccttacaaggagagaaaaagcaccgtgcatgccgatt
    ggtggaagtaaggtggtacgatcgtgccttattaggaaggcaacagacgggtctgacatggattggacgaaccactgaattgccgcattgcagagat
    attgtatttaagtgcctagctcgatacataaacgggtctctctggttagaccagatctgagcctgggagctctctggctaactagggaacccactgctta
    agcctcaataaaagcttgccttgagtgcttcaagtagtgtgtgcccgtctgttgtgtgactctggtaactagagatccctcagacccttttagtcagtgtgg
10  aaaatctctagcagtggcgcccgaacagggacttgaaagcgaaagggaaaccagaggagctctctcgacgcaggactcggcttgctgaagcgcg
    cacggcaagaggcgaggggcggcgactggtgagtacgccaaaaattttgactagcggaggctagaaggagagagatgggtgcgagagcgtcag
    tattaagcgggggagaattagatcgcgatgggaaaaaattcggttaaggccaggggganagaaaaaatataaattaaaacatatagtatgggcaag
    cagggagctagaacgattcgcagttaatcctggcctgttagaaacatcagaaggctgtagacaaatactgggacagctacaaccatcccttcagaca
    ggatcagaagaacttagatcattatataatacagtagcaaccctctattgtgtgcatcaaaggatagagataaaagacaccaaggaagctttagacaa
15  gatagaggaagagcaaaacaaaagtaagaccaccgcacagcaagcggccgctgatcttcagacctggaggaggagatatgagggacaattgga
    gaagtgaattatataaatataagtagtaaaaattgaaccattaggagtagcacccaccaaggcaaagagaagagtggtgcagagagaaaaaagag
    cagtgggaataggagctttgttccttgggttcttgggagcagcaggaagcactatgggcgcagcgtcaatgacgctgacggtacaggccagacaat
    tattgtctggtatagtgcagcagcagaacaatttgctgagggctattgaggcgcaacagcatctgttgcaactcacagtctggggcatcaagcagctc
    caggcaagaatcctggctgtggaaagatacctaaaggatcaacagctcctggggatttggggttgctctggaaaactcatttgcaccactgctgtgcc
20  ttggaatgctagttggagtaataaatctctgaacagatttggaatcacacgacctggatggagtgggacagagaaattaacaattacacaagcttaat
    acactccttaattgaagaatcgcaaaaccagcaagaaaagaatgaacaagaattattggaattagataaatgggcaagtttgtggaattggtttaacat
    aacaaattggctgtggtatataaaattattcataatgatagtaggaggcttggtaggtttaagaatagttttgctgtactttctatagtgaatagagttagg
    cagggatattcaccattatcgtttcagacccacctcccaaccccgaggggacccgacaggcccgaaggaatagaagaagaaggtggagagagag
    acagagacagatccattcgattagtgaacggatctcgacggtaatcgattttcccatgattccttcatatttgcatatacgatacaaggctgttagagaga
25  taattagaattaatttgactgtaaacacaaagatattagtacaaaatacgtgacgtagaaagtaataatttcttgggtagtttgcagttttaaaattatgtttt
    aaaatggactatcatatgcttaccgtaacttgaaagtatttcgatttcttggctttatatatcttgtggaaaggacgaaacaccgaattcaccggtcggtta
    gtaatgagtttggaattaattctgtggaatgtgtgtcagttagggtgtggaaagtccccaggctccccaggcaggcagaagtatgcaaagcatgcatct
    caattagtcagcaaccaggtgtggaaagtccccaggctccccagcaggcagaagtatgcaaagcatgcatctcaattagtcagcaaccatagtccc
    gcccctaactccgcccatcccgcccctaactccgcccagttccgcccattctccgccccatggctgactaattttttttatttatgcagaggccgaggc
30  cgcctctgcctctgagctattccagaagtagtgaggaggcttttttggaggcctaggcttttgcaaaaagctcccgggatggtgagcaagcagatcct
    gaagaacaccggcctgcaggagatcatgagcttcaaggtgaacctggagggcgtggtgaacaaccacgtgttcaccatggagggctgcggcaag
    ggcaacatcctgttcggcaaccagctggtgcagatccgcgtgaccaagggcgcccccctgcccttcgccttcgacatcctgagccccgccttccag
    tacggcaaccgcaccttcaccaagtaccccgaggacatcagcgacttcttcatccagcttccccgccggcttcgtgtacgagcgcaccctgcgct
    acgaggacggcggcctggtggagatccgcagcgacatcaacctgatcgaggagatgttcgtgtaccgcgtggagtacaagggccgcaacttccc
35  caacgacggccccgtgatgaagaagaccatcaccggcctgcagcccagcttcgaggtggtgtacatgaacgacggcgtgctggtgggccaggtg
    atcctggtgtaccgcctgaacagcggcaagttctacagctgccacatgcgcacccctgatgaagagcaagggcgtggtgaaggacttccccgagta
    ccacttcatccagcaccgcctggagaagacctacgtggaggacggcggcttcgtggagcagcacgagaccgccatcgcccagctgaccagcctg
    ggcaagcccctgggcagcctgcacgagtgggtgtaaggtaccttttaagaccaatgacttacaaggcagctgtagatcttagccacttttaaaagaaa
    aggggggactggaagggctaattcactcccaacgaagacaagatctgcttttttgcttgtactgggtctctctggttagaccagatctgagcctgggag
40  ctctctggctaactagggaacccactgcttaagcctcaataaagcttgccttgagtgcttcaagtagtgtgtgcccgtctgttgtgtgactctggtaacta
    gagatccctcagacccttttagtcagtgtggaaaatctctagcagtagtagttcatgtcatcttattattcagtatttataacttgcaaagaaatgaatatca
    gagagtgagaggaacttgtttattgcagcttataatggttacaaataaagcaatagcatcacaaatttcacaaataaagcatttttttcactgcattctagtt
    gtggtttgtccaaactcatcaatgtatcttatcatgtctggctctagctatcccgcccctaactccgcccatcccgcccctaactccgcccagttccgcc
    cattctccgccccatggctgactaattttttttatttatgcagaggccgaggccgcctcggcctctgagctattccagaagtagtgaggaggctttttgg
45  aggcctaggacgtacccaattcgccctatagtgagtcgtattacgcgcgctcactggccgtcgttttacaacgtcgtgactgggaaaaccctggcgt
    tacccaacttaatcgccttgcagcacatccccctttcgccagctggcgtaatagcgaagaggcccgcaccgatcgcccttcccaacagttgcgcagc
    ctgaatggcgaatgggacgcgccctgtagcggcgcattaagcgcggcgggtgtggtggttacgcgcagcgtgaccgctacacttgccagc

FIGURE 2 (CONT.)

```
     gccctagcgcccgctcctttcgctttcttcccttcctttctcgccacgttcgccggctttccccgtcaagctctaaatcgggggctcccttttagggttccg
  5  atttagtgctttacggcacctcgaccccaaaaaacttgattagggtgatggttcacgtagtgggccatcgccctgatagacggttttcgcccttttgacgt
     tggagtccacgttctttaatagtggactcttgttccaaactggaacaacactcaaccctatctcggtctattctttttgatttataagggattttgccgatttcg
     gcctattggttaaaaaatgagctgatttaacaaaaatttaacgcgaattttaacaaaatattaacgcttacaattttaggtggcacttttcggggaaatgtgc
     gcggaaccccctatttgtttattttttctaaatacattcaaatatgtatccgctcatgagacaataaccctgataaatgcttcaataatattgaaaaaggaaga
     gtatgagtattcaacatttccgtgtcgcccttattcccttttttgcggcatttttgccttcctgtttttgctcacccagaaacgctggtgaaagtaaaagatgct
 10  gaagatcagttgggtgcacgagtgggttacatcgaactggatctcaacagcggtaagatccttgagagttttcgccccgaagaacgttttccaatgat
     gagcacttttaaagttctgctatgtggcgcggtattatcccgtattgacgccgggcaagagcaactcggtcgccgcatacactattctcagaatgactt
     ggttgagtactcaccagtcacagaaaagcatcttacggatggcatgacagtaagagaattatgcagtgctgccataaccatgagtgataacactgcg
     gccaacttacttctgacaacgatcggaggaccgaaggagctaaccgcttttttgcacaacatgggggatcatgtaactcgccttgatcgttgggaacc
     ggagctgaatgaagccataccaaacgacgagcgtgacaccacgatgcctgtagcaatggcaacaacgttgcgcaaactattaactggcgaactact
 15  tactctagcttcccggcaacaattaatagactggatggaggcggataaagttgcaggaccacttctgcgctcggcccttccggctggctggtttattgc
     tgataaatctggagccggtgagcgtgggtctcgcggtatcattgcagcactggggccagatggtaagccctcccgtatcgtagttatctacacgacg
     gggagtcaggcaactatgatgaacgaaatagacagatcgctgagataggtgcctcactgattaagcattggtaactgtcagaccaagtttactcata
     tatactttagattgatttaaaacttcattttttaattaaaaggatctaggtgaagatccttttttgataatctcatgaccaaaatcccttaacgtgagttttcgttc
     cactgagcgtcagaccccgtagaaaagatcaaaggatcttcttgagatccttttttttctgcgcgtaatctgctgcttgcaaacaaaaaaaccaccgcta
 20  ccagcggtggtttgtttgccggatcaagagctaccaactcttttttccgaaggtaactggcttcagcagagcgcagataccaaatactgttcttctagtgt
     agccgtagttaggccaccacttcaagaactctgtagcaccgcctacatacctcgctctgctaatcctgttaccagtggctgctgccagtggcgataagt
     cgtgtcttaccgggttggactcaagacgatagttaccggataaggcgcagcggtcgggctgaacggggggttcgtgcacacagcccagcttggag
     cgaacgacctacaccgaactgagatacctacagcgtgagctatgagaaagcgccacgcttcccgaagggagaaaggcggacaggtatccggtaa
     gcggcagggtcggaacaggagagcgcacgagggagcttccaggggaaacgcctggtatctttatagtcctgtcgggtttcgccacctctgacttg
 25  agcgtcgatttttgtgatgctcgtcaggggggcggagcctatggaaaaacgccagcaacgcggcctttttacggttcctggccttttgctggccttttgc
     tcacatgttctttcctgcgttatcccctgattctgtggataaccgtattaccgcctttgagtgagctgataccgctcgccgcagccgaacgaccgagcgc
     agcgagtcagtgagcgaggaagcggaagagcgcccaatacgcaaaccgcctctccccgcgcgttggccgattcattaatgcagctggcacgaca
     ggtttcccgactggaaagcgggcagtgagcgcaacgcaattaatgtgagttagctcactcattaggcaccccaggctttacactttatgcttccggctc
     gtatgttgtgtggaattgtgagcggataacaatttcacacaggaaacagctatgaccatgattacgccaagcgcgcaattaaccctcactaaagggaa
 30  caaaagctggagctgcaagctt
```

FIGURE 3

MSCV-U6-Hygro tgaaagaccccacctgtaggtttggcaagctagcttaagtaacgccattttgcaaggcatggaaaatacataactgagaatagagaagttcagatcaa
ggttaggaacagagagacagcagaatatgggccaaacaggatatctgtggtaagcagttcctgccccggctcagggccaagaacagatggtccc
agatgcggtcccgccctcagcagtttctagagaaccatcagatgtttccagggtgccccaaggacctgaaatgaccctgtgccttatttgaactaacc
aatcagttcgcttctcgcttcgttcgcgcgcgcttctgctccccgagctcaataaaagagcccacaacccctcactcggcgcgccagtcctccgataga
ctgcgtcgcccgggtacccgtattcccaataaaagcctcttgctgtttgcatccgaatcgtggactcgctgatccttgggagggtctcctcagattgattg
actgccacctcggggggtctttcatttggaggttccaccgagatttggagaccctgcccagggaccaccgaccccccccgccgggaggtaagctg
gccagcggtcgtttcgtgtctgtctctgtcttttgtgcgtgtttgtgccggcatctaatgtttgcgcctgcgtctgtactagttagctaactagctctgtatctg
gcggacccgtggtggaactgacgagttctgaacacccggccgcaaccctgggagacgtcccagggacttttgggggccgttttttgtggcccgacct
gaggaagggagtcgatgtggaatccgacccccgtcaggatatgtggttctggtaggagacgagaacctaaaacagttcccgcctccgtctgaattttt
gctttcggtttggaaccgaagccgcgcgtcttgtctgctgcagcgctgcagcatcgttctgtgttgtctctgtctgactgtgtttctgtatttgtctgaaaatt
agggccagactgttaccactcccttaagtttgaccttaggtcactggaaagatgtcgagcggatcgctcacaaccagtcggtagatgtcaagaagag
acgttgggttaccttctgctctgcagaatggccaaccttttaacgtcggatggccgcgagacggcacctttaaccgagacctcatcacccaggttaaga
tcaaggtcttttcacctggcccgcatggacacccagaccaggtcccctacatcgtgacctgggaagccttggcttttgaccccccctccctgggtcaag
ccctttgtacacccctaagcctccgcctcctcttcctccatccgccccgtctctcccccttgaacctcctcgttcgaccccgcctcgtatcctccctttatcc
agccctcactccttctctaggcgccggaattagatctttcccatgattccttcatatttgcatatacgatacaaggctgttagagagataattagaattaatt
tgactgtaaacacaaagatattagtacaaaatacgtgacgtagaaagtaataattcttgggtagtttgcagttttttaaaattatgttttaaaatggactatc
atatgcttaccgtaacttgaaagtatttcgatttcttggctttatatatcttgtggaaaggacgaaacacctctgaggttaacggatccgcggccgcacgc
gtgttaacgaattctaccgggtagggggaggcgcttttcccaaggcagtctggagcatgcgctttagcagccccgctgggcacttggcgctacacaag
tggcctctgtgcctcgcacacattccacatccaccggtaggcgccaaccggctccgttctttggtggcccccttcgcgccaccttctactcctcccctagt
caggaagttccccccccgccccgcagctcgcgtcgtgcaggacgtgacaaatggaagtagcacgtctcactagtctcgtgcagatggacagcaccg
ctgagcaatggaagcgggtaggcctttggggcagcggccaatagcagctttgctccttcgctttctgggctcagaggctgggaaggggtgggtccg
ggggcgggctcaggggcgggctcaggggcggggcgggcgcccgaaggtcctccggaggcccggcattctgcacgcttcaaaagcgcacgtct
gccgcgctgttctcctcttcctcatctccgggcctttcgacctgcatcccgccaccatgaaaaagcctgaactcaccgcgacgtctgtcgagaagtttc
tgatcgaaaagttcgacagcgtctccgacctgatgcagctctcggagggcgaagaatctcgtgctttcagcttcgatgtaggagggcgtggatatgtc
ctgcgggtaaatagctgcgccgatggtttctacaaagatcgttatgtttatcggcactttgcatcggccgcgctcccgattccgaagtgcttgacattg
gggaattcagcgagagcctgacctattgcatctcccgccgtgcacagggtgtcacgttgcaagacctgcctgaaaccgaactgcccgctgttctgca
gccggtcgcggaggccatggatgcgatcgctgcggccgatcttagccagacgagcgggttcggcccattcggaccgcaaggaatcggtcaatac
actacatggcgtgatttcatatgcgcgattgctgatccccatgtgtatcactggcaaactgtgatggacgacaccgtcagtgcgtccgtcgcgcaggct
ctcgatgagctgatgctttgggccgaggactgccccgaagtccggcacctcgtgcacgcggatttcggctccaacaatgtcctgacggacaatggc
cgcataacagcggtcattgactggagcgaggcgatgttcggggattcccaatacgaggtcgccaacatcttcttctggaggccgtggttggcttgtat
ggagcagcagacgcgctacttcgagcggaggcatccggagcttgcaggatcgccgcggctccggggcgtatatgctccgcattggtcttgaccaa
ctctatcagagcttggttgacggcaatttcgatgatgcagcttgggcgcagggtcgatgcgacgcaatcgtccgatccggagccgggactgtcggg
cgtacacaaatcgcccgcagaagcgcggccgtctggaccgatggctgtgtagaagtactcgccgatagtggaaaccgacgccccagcactcgtc
cgagggcaaaggaatagagtagatgccgaccgaacaagagctgatttcgagaacgcctcagccagcaactcgcgcgagcctagcaaggcaaat
gcgagagaacggccttacgcttggtggcacagttctcgtccacagttcgctaagctcgctcggctgggtcgcgggagggccggtcgcagtgattca
ggccttctggattgttggtccccagggcacgattgtcatgcccacgcactcgggtgatctgactgatcccgcagattggagatcgccgcccgtg
cctgccgattgggtgcagatccgtcgacctgcagccaagcttatcgataaaataaaagattttatttagtctccagaaaaagggggggaatgaaagacc
ccacctgtaggtttggcaagctagcttaagtaacgccattttgcaaggcatggaaaatacataactgagaatagagaagttcagatcaaggttaggaa
cagagagacagcagaatatgggccaaacaggatatctgtggtaagcagttcctgccccggctcagggccaagaacagatggtccccagatgcggt
cccgcccctcagcagtttctagagaaccatcagatgtttccagggtgccccaaggacctgaaatgaccctgtgccttatttgaactaaccaatcagttcg
cttctcgcttctgttcgcgcgcttctgctccccgagctcaataaaagagcccacaacccctcactcggcgcgccagtcctccgatagactgcgtcgcc
cgggtacccgtgtatccaataaaccctcttgcagttgcatccgacttgtggtctcgctgttccttgggaggggtctcctctgagtgattgactaccgtca
gcgggggtctttcatgggtaacagtttcttgaagttggagaacaacattctgagggtaggagtcgaatattaagtaatcctgactcaattagccactgttt
tgaatccacatactccaatactcctgaaatagttcattatggacagcgcagaagagctggggagaattaattcgtaatca

FIGURE 3 (CONT.)

```
   tggtcatagctgtttcctgtgtgaaattgttatccgctcacaattccacacaacatacgagccggaagcataaagtgtaaagcctggggtgcctaatga
   gtgagctaactcacattaattgcgttgcgctcactgcccgctttccagtcgggaaacctgtcgtgccagctgcattaatgaatcggccaacgcgcggg
5  gagaggcggtttgcgtattgggcgctcttccgcttcctcgctcactgactcgctgcgctcggtcgttcggctgcggcgagcggtatcagctcactcaa
   aggcggtaatacggttatccacagaatcaggggataacgcaggaaagaacatgtgagcaaaaggccagcaaaaggccaggaaccgtaaaaagg
   ccgcgttgctggcgtttttccataggctccgcccccctgacgagcatcacaaaaatcgacgctcaagtcagaggtggcgaaacccgacaggactat
   aaagataccaggcgtttccccctggaagctccctcgtgcgctctcctgttccgaccctgccgcttaccggatacctgtccgcctttctcccttcgggaa
   gcgtggcgctttctcatagctcacgctgtaggtatctcagttcggtgtaggtcgttcgctccaagctgggctgtgtgcacgaaccccccgttcagcccg
10 accgctgcgccttatccggtaactatcgtcttgagtccaacccggtaagacacgacttatcgccactggcagcagccactggtaacaggattagcag
   agcgaggtatgtaggcggtgctacagagttcttgaagtggtggcctaactacggctacactagaaggacagtatttggtatctgcgctctgctgaagc
   cagttaccttcggaaaaagagttggtagctcttgatccggcaaacaaaccaccgctggtagcggtggtttttttgtttgcaagcagcagattacgcgca
   gaaaaaaaggatctcaagaagatcctttgatcttttctacggggtctgacgctcagtggaacgaaaactcacgttaagggattttggtcatgagattatc
   aaaaaggatcttcacctagatcctttaaattaaaaatgaagttttaaatcaatctaaagtatatatgagtaaacttggtctgacagttaccaatgcttaatc
15 agtgaggcacctatctcagcgatctgtctatttcgttcatccatagttgcctgactccccgtcgtgtagataactacgatacgggagggcttaccatctg
   gccccagtgctgcaatgataccgcgagacccacgctcaccggctccagatttatcagcaataaaccagccagccggaagggccgagcgcagaag
   tggtcctgcaactttatccgcctccatccagtctattaattgttgccgggaagctagagtaagtagttcgccagttaatagtttgcgcaacgttgttgccat
   tgctacaggcatcgtggtgtcacgctcgtcgtttggtatggcttcattcagctccggttcccaacgatcaaggcgagttacatgatcccccatgttgtgc
   aaaaaagcggttagctccttcggtcctccgatcgttgtcagaagtaagttggccgcagtgttatcactcatggttatggcagcactgcataattctcttac
20 tgtcatgccatccgtaagatgcttttctgtgactggtgagtactcaaccaagtcattctgagaatagtgtatgcggcgaccgagttgctcttgcccggcg
   tcaatacgggataataccgcgccacatagcagaactttaaaagtgctcatcattggaaaacgttcttcggggcgaaaactctcaaggatcttaccgct
   gttgagatccagttcgatgtaacccactcgtgcacccaactgatcttcagcatcttttactttcaccagcgtttctgggtgagcaaaaacaggaaggca
   aaatgccgcaaaaaagggaataagggcgacacggaaatgttgaatactcatactcttcctttttcaatattattgaagcatttatcagggttattgtctcat
   gagcggatacatatttgaatgtatttagaaaaataaacaaatagggggttccgcgcacatttccccgaaaagtgccacctgacgtctaagaaaccattat
25 tatcatgacattaacctataaaaataggcgtatcacgaggccctttcgtctcgcgcgtttcggtgatgacggtgaaaacctctgacacatgcagctccc
   ggagacggtcacagcttgtctgtaagcggatgccgggagcagacaagcccgtcagggcgcgtcagcgggtgttggcgggtgtcggggctggctt
   aactatgcggcatcagagcagattgtactgagagtgcaccatatgcggtgtgaaataccgcacagatgcgtaaggagaaaataccgcatcaggcgc
   cattcgccattcaggctgcgcaactgttgggaagggcgatcggtgcgggcctcttcgctattacgccagctggcgaaaggggggatgtgctgcaagg
   cgattaagttgggtaacgccagggttttcccagtcacgacgttgtaaaacgacggcgcaaggaatggtgcatgcaaggagatggcgcccaacagtc
30 ccccggccacggggcctgccaccatacccacgccgaaacaagcgctcatgagcccgaagtggcgagcccgatcttccccatcggtgatgtcggc
   gatataggcgccagcaaccgcacctgtggcgccggtgatgccggccacgatgcgtccggcgtagaggcgattagtccaatttgttaaagacaggat
   atcagtggtccaggctctagttttgactcaacaatatcaccagctgaagcctatagagtacgagccatagataaaataaaagattttatttagtctccag
   aaaaaggggggaa
35
```

FIGURE 4

MSCV-U6-Puro 5  tgaaagaccccacctgtaggtttggcaagctagcttaagtaacgccattttgcaaggcatggaaaatacataactgagaatagagaagttcagatcaa
ggttaggaacagagagacagcagaatatgggccaaacaggatatctgtggtaagcagttcctgccccggctcagggccaagaacagatggtcccc
agatgcggtcccgccctcagcagtttctagagaaccatcagatgtttccagggtgccccaaggacctgaaatgaccctgtgccttatttgaactaacc
aatcagttcgcttctcgcttctgttcgcgcgcttctgctccccgagctcaataaaagagcccacaaccccctcactcggcgcgccagtcctccgataga
ctgcgtcgcccgggtacccgtattcccaataaagcctcttgctgtttgcatccgaatcgtggactcgctgatccttgggagggtctcctcagattgattg
10 actgcccacctcgggggtctttcatttggaggttccaccgagatttggagaccccctgcccagggaccaccgaccccccgccgggaggtaagctg
gccagcggtcgtttcgtgtctgtctctgtctttgtgcgtgtttgtgccggcatctaatgtttgcgcctgcgtctgtactagttagctaactagctctgtatctg
gcggacccgtggtggaactgacgagttctgaacacccggccgcaaccctgggagacgtcccagggactttgggggccgttttttgtggcccgacct
gaggaagggagtcgatgtggaatccgaccccgtcaggatatgtggttctggtaggagacgagaacctaaaacagttcccgcctccgtctgaattttt
gctttcggtttggaaccgaagccgcgcgtcttgtctgctgcagcgctgcagcatcgttctgtgttgtctctgtctgactgtgttctgtatttgtctgaaaatt
15 agggccagactgttaccactcccttaagtttgaccttaggtcactggaaagatgtcgagcggatcgctcacaaccagtcggtagatgtcaagaagag
acgttgggttaccttctgctctgcagaatggccaaccttaacgtcggatggccgcgagacggcacctttaaccgagacctcatcacccaggttaaga
tcaaggtcttttcacctggcccgcatggacacccagaccaggtcccctacatcgtgacctgggaagccttggcttttgaccccccctccctgggtcaag
cccttttgtacacccctaagcctccgcctcctcttcctccatccgccccgtctctccccttgaacctcctcgttcgaccccgcctcgatcctccctttatcc
agccctcactccttctctaggcgccggaattagatctttcccatgattccttcatatttgcatatacgatacaaggctgttagagagataattagaattaatt
20 tgactgtaaacacaaagatattagtacaaaatacgtgacgtagaaagtaataatttcttgggtagtttgcagttttaaaattatgttttaaaatggactatc
atatgcttaccgtaacttgaaagtatttcgatttcttggctttatatatcttgtggaaaggacgaaacacctctgaggttaacggatccgcgccgcacgc
gtgttaacgaattctaccgggtaggggaggcgcttttcccaaggcagtctgggagcatgcgctttagcagccccgctgggcacttggcgctacacaag
tggcctctgcctcgcacacattccacatccaccggtaggcgccaaccggctccgttctttggtggcccttcgcgccaccttctactcctcccctagt
caggaagttcccccccgccccgcagctcgcgtcgtgcaggacgtgacaaatggaagtagcacgtctcactagtctcgtgcagatggacagcaccg
25 ctgagcaatggaagcgggtaggcctttggggcagcggccaatagcagctttgctccttcgctttctgggctcagaggctgggaaggggtgggtccg
ggggcgggctcaggggcgggctcaggggcggggcgggcgcccgaaggtcctccggaggcccggcattctgcacgcttcaaaagcgcacgtct
gccgcgctgttctcctcttcctcatctccgggcctttcgacctgcagcccaagcttaccatgaccgagtacaagcccacggtgcgcctcgccacccg
cgacgacgtccccagggccgtacgcaccctcgccgccgcgttcgccgactaccccgccacgcgccacaccgtcgatccggaccgccacatcga
gcgggtcaccgagctgcaagaactcttcctcacgcgcgtcgggctcgacatcggcaaggtgtgggtcgcggacgacggcgccgcggtggcggtc
30 tggaccacgccggagagcgtcgaagcgggggcggtgttcgccgagatcggcccgcgcatggccgagttgagcggttcccggctggccgcgca
gcaacagatggaaggcctcctggcgccgcaccggcccaaggagcccgcgtggttcctggccaccgtcggcgtctcgcccgaccaccagggcaa
gggtctgggcagcgccgtcgtgctccccggagtggaggcggccgagcgcgccggggtgcccgccttcctggagacctccgcgccccgcaacct
cccttctacgagcggctcggcttcaccgtcaccgccgacgtcgaggtgcccgaaggaccgcgcacctggtgcatgacccgcaagcccggtgcc
tgacgcccgccccacgacccgcagcgcccgaccgaaaggagcgcacgaccccatgcatcgataaaataaaagattttatttagtctccagaaaaa
35 ggggggaatgaaagaccccacctgtaggtttggcaagctagcttaagtaacgccattttgcaaggcatggaaaatacataactgagaatagagaagt
tcagatcaaggttaggaacagagagacagcagaatatgggccaaacaggatatctgtggtaagcagttcctgccccggctcagggccaagaacag
atggtcccccagatgcggtcccgccctcagcagtttctagagaaccatcagatgtttccagggtgccccaaggacctgaaatgaccctgtgccttattt
gaactaaccaatcagttcgcttctcgcttctgttcgcgcgcttctgctccccgagctcaataaaagagcccacaaccccctcactcggcgcgccagtcc
tccgatagactgcgtcgcccgggtacccgtgtatccaataaagccctcttgcagttgcatccgacttgtggtctcgctgttccttgggagggtctcctctg
40 agtgattgactacccgtcagcggggtctttcatgggtaacagtttcttgaagttggagaacaacattctgagggtaggagtcgaatattaagtaatcct
gactcaattagccactgttttgaatccacatactccaatactcctgaaatagttcattatggacagcgcagaagagctggggagaattaattcgtaatca
tggtcatagctgtttcctgtgtgaaattgttatccgctcacaattccacacaacatacgagccggaagcataaagtgtaaagcctggggtgcctaatga
gtgagctaactcacattaattgcgttgcgctcactgcccgctttccagtcgggaaacctgtcgtgccagctgcattaatgaatcggccaacgcgcggg
gagaggcggtttgcgtattgggcgctcttccgcttcctcgctcactgactcgctgcgctcggtcgttcggctgcggcgagcggtatcagctcactcaa
45 aggcggtaatacggttatccacagaatcaggggataacgcaggaaagaacatgtgagcaaaaggccagcaaaaggccaggaaccgtaaaaagg
ccgcgttgctggcgtttttccataggctccgcccccctgacgagcatcacaaaaatcgacgctcaagtcagaggtggcgaaacccgacaggactat

FIGURE 4 (CONT.)

```
 5  aaagataccaggcgtttccccctggaagctccctcgtgcgctctcctgttccgaccctgccgcttaccggatacctgtccgcctttctcccttcggga
    gcgtggcgcttctcatagctcacgctgtaggtatctcagttcggtgtaggtcgttcgctccaagctgggctgtgtgcacgaa
    cccccgttcagcccgaccgctgcgccttatccggtaactatcgtcttgagtccaacccggtaagacacgacttatcgccactggcagcagccactg
    gtaacaggattagcagagcgaggtatgtaggcggtgctacagagttcttgaagtggtggcctaactacggctacactagaaggacagtatttggtatc
    tgcgctctgctgaagccagttaccttcggaaaaagagttggtagctcttgatccggcaaacaaaccaccgctggtagcggtggtttttttgtttgcaagc
10  agcagattacgcgcagaaaaaaaggatctcaagaagatcctttgatcttttctacggggtctgacgctcagtggaacgaaaactcacgttaagggatt
    ttggtcatgagattatcaaaaaggatcttcacctagatcctttaaattaaaaatgaagttttaaatcaatctaaagtatatatgagtaaacttggtctgaca
    gttaccaatgcttaatcagtgaggcacctatctcagcgatctgtctatttcgttcatccatagttgcctgactccccgtcgtgtagataactacgatacgg
    gagggcttaccatctggccccagtgctgcaatgataccgcgagacccacgctcaccggctccagatttatcagcaataaaccagccagccggaag
    ggccgagcgcagaagtggtcctgcaactttatccgcctccatccagtctattaattgttgccgggaagctagagtaagtagttcgccagttaatagtttg
15  cgcaacgttgttgccattgctacaggcatcgtggtgtcacgctcgtcgtttggtatggcttcattcagctccggttcccaacgatcaaggcgagttacat
    gatcccccatgttgtgcaaaaaagcggttagctccttcggtcctccgatcgttgtcagaagtaagttggccgcagtgttatcactcatggttatggcagc
    actgcataattctcttactgtcatgccatccgtaagatgcttttctgtgactggtgagtactcaaccaagtcattctgagaatagtgtatgcggcgaccga
    gttgctcttgcccggcgtcaatacgggataataccgcgccacatagcagaactttaaaagtgctcatcattggaaaacgttcttcggggcgaaaactct
    caaggatcttaccgctgttgagatccagttcgatgtaacccactcgtgcacccaactgatcttcagcatcttttactttcaccagcgtttctgggtgagca
20  aaaacaggaaggcaaaatgccgcaaaaaagggaataagggcgacacggaaatgttgaatactcatactcttcctttttcaatattattgaagcatttat
    cagggttattgtctcatgagcggatacatatttgaatgtatttagaaaaataaacaaataggggttccgcgcacatttccccgaaaagtgccacctgac
    gtctaagaaaccattattatcatgacattaacctataaaaataggcgtatcacgaggccctttcgtctcgcgcgtttcggtgatgacggtgaaaacctct
    gacacatgcagctcccggagacggtcacagcttgtctgtaagcggatgccgggagcagacaagcccgtcagggcgcgtcagcgggtgttggcgg
    gtgtcggggctggcttaactatgcggcatcagagcagattgtactgagagtgcaccatatgcggtgtgaaataccgcacagatgcgtaaggagaaa
25  ataccgcatcaggcgccattcgccattcaggctgcgcaactgttggggaagggcgatcggtgcgggcctcttcgctattacgccagctggcgaaagg
    gggatgtgctgcaaggcgattaagttgggtaacgccagggttttcccagtcacgacgttgtaaaacgacggcgcaaggaatggtgcatgcaaggag
    atggcgcccaacagtcccccggccacggggcctgccaccatacccacgccgaaacaagcgctcatgagcccgaagtggcgagcccgatcttcc
    ccatcggtgatgtcggcgatataggcgccagcaaccgcacctgtggcgccggtgatgccggccacgatgcgtccggcgtagaggcgattagtcca
    atttgttaaagacaggatatcagtggtccaggctctagttttgactcaacaatatcaccagctgaagcctatagagtacgagccatagataaaataaaa
30  gattttatttagtctccagaaaaagggggaa
```

FIGURE 5

MSCV-U6-hrGFP 5   tgaaagaccccacctgtaggtttggcaagctagcttaagtaacgccattttgcaaggcatggaaaatacataactgagaatagagaagttcagatcaa
    ggttaggaacagagagacagcagaatatgggccaaacaggatatctgtggtaagcagttcctgccccggctcagggccaagaacagatggtcccc
    agatgcggtcccgccctcagcagtttctagagaaccatcagatgtttccagggtgccccaaggacctgaaatgaccctgtgccttatttgaactaacc
    aatcagttcgcttctcgcttctgttcgcgcgcgcttctgctccccgagctcaataaaagagcccacaaccccctcactcggcgcgccagtcctccgataga
    ctgcgtcgcccgggtacccgtattcccaataaagcctcttgctgtttgcatccgaatcgtggactcgctgatccttgggagggtctcctcagattgattg
10  actgccacctcggggtctttcatttggaggttccaccgagatttggagaccctgcccagggaccaccgaccccccgccgggaggtaagctg
    gccagcggtcgtttcgtgtctgtctctgtctttgtgcgtgtttgtgccggcatctaatgtttgcgcctgcgtctgtactagttagctaactagctctgtatctg
    gcggacccgtggtggaactgacgagttctgaacacccggccgcaaccctgggagacgtcccagggactttgggggccgtttttgtggcccgacct
    gaggaagggagtcgatgtggaatccgaccccgtcaggatatgtggttctggtaggagacgagaacctaaaacagttcccgcctccgtctgaattttt
    gctttcggtttggaaccgaagccgcgcgtcttgtctgctgcagcgctgcagcatcgttctgtgttgtctctgtctgactgtgtttctgtatttgtctgaaaatt
15  agggccagactgttaccactccctttaagtttgaccttaggtcactggaaagatgtcgagcggatcgctcacaaccagtcggtagatgtcaagaagag
    acgttgggttaccttctgctctgcagaatggccaaccttttaacgtcggatggccgcgagacggcacctttaaccgagacctcatcacccaggttaaga
    tcaaggtcttttcacctggcccgcatggacacccagaccaggtccctacatcgtgacctgggaagccttggcttttgaccccctccctgggtcaag
    cccttttgtacaccctaagcctccgcctcctcttcctccatccgccccgtctctcccccttgaacctcctcgttcgaccccgcctcgtatcctcccttatcc
    agccctcactccttctctaggcgccggaattagatctttccatgattccttcatatttgcatatacgatacaaggctgttagagagataattagaattaat
20  tgactgtaaacacaaagatattagtacaaaatacgtgacgtagaaagtaataattcttgggtagtttgcagttttaaaattatgttttaaaatggactatc
    atatgcttaccgtaacttgaaagtatttcgatttcttggctttatatatcttgtggaaaggacgaaacacctctgaggttaacggatccgcggccgcacgc
    gtctgtggaatgtgtgtcagttagggtgtggaaagtccccaggctccccaggcaggcagaagtatgcaaagcatgcatctcaattagtcagcaacca
    ggtgtggaaagtccccaggctccccagcaggcagaagtatgcaaagcatgcatctcaattagtcagcaaccatagtcccgcccctaactccgccca
    tcccgcccctaactccgcccagttccgcccattctccgccccatggctgactaatttttttattatgcagaggccgaggccgcctctgcctctgagct
25  attccagaagtagtgaggaggcttttttggaggcctaggcttttgcaaaaagctcccgggatggtgagcaagcagatcctgaagaacaccggcctgc
    aggagatcatgagcttcaaggtgaacctggagggcgtggtgaacaaccacgtgttcaccatgagagggctgcggcaagggcaacatcctgttcggc
    aaccagctggtgcagatccgcgtgaccaagggcgccccctgccttcgccttcgacatcctgagccccgccttccagtacggcaaccgcaccttc
    accaagtaccccgaggacatcagcgacttcttcatccagagcttcccgccggcttcgtgtacgagcgcaccctgcgctacgagacggcggcct
    ggtggagatccgcagcgacatcaacctgatcgaggagatgttcgtgtaccgcgtggagtacaaggccgcaacttccccaacgacggccccgtga
30  tgaagaagaccatcaccgcctgcagcccagcttcgaggtggtgtacatgaacgacggcgtgctggtgggccaggtgatcctggtgtaccgcctg
    aacagcggcaagttctacagctgccacatgcgcaccctgatgaagagcaagggcgtggtgaaggacttccccgagtaccacttcatccagcaccg
    cctggagaagacctacgtggaggacggcggcttcgtggagcagcacgagaccgccatcgcccagctgaccagcctgggcaagcccctgggca
    gcctgcacgagtgggtgtaagtcgacctgcagccaagcttatcgataaaataaaagattttatttagtctccagaaaaaggggggaatgaaagaccc
    cacctgtaggtttggcaagctagcttaagtaacgccattttgcaaggcatggaaaatacataactgagaatagagaagttcagatcaaggttaggaac
35  agagagacagcagaatatgggccaaacaggatatctgtggtaagcagttcctgccccggctcagggccaagaacagatggtccccagatgcggtc
    ccgccctcagcagtttctagagaaccatcagatgtttccagggtgccccaaggacctgaaatgaccctgtgccttatttgaactaaccaatcagttcgc
    ttctcgcttctgttcgcgcgcttctgctccccgagctcaataaaagagcccacaaccccctcactcggcgcgccagtcctccgatagactgcgtcgccc
    gggtacccgtgtatccaataaaccctcttgcagttgcatccgacttgtggtctcgctgttccttgggagggtctcctctgagtgattgactaccgtcag
    cgggggtctttcatgggtaacagtttcttgaagtggagaacaacattctgagggtaggagtcgaatattaagtaatcctgactcaattagccactgtttt
40  gaatccacatactccaatactcctgaaatagttcattatggacagcgcagaagagctggggagaattaattcgtaatcatggtcatagctgtttcctgtg
    tgaaattgttatccgctcacaattccacacaacatacgagccggaagcataaagtgtaaagcctggggtgcctaatgagtgagctaactcacattaatt
    gcgttgcgctcactgcccgctttccagtcgggaaacctgtcgtgccagctgcattaatgaatcggccaacgcgcggggagaggcggtttgcgtattg
    ggcgctcttccgcttcctcgctcactgactcgctgcgctcggtcgttcggctgcggcgagcggtatcagctcactcaaaggcggtaatacggttatcc
    acagaatcaggggataacgcaggaaagaacatgtgagcaaaaggccagcaaaaggccaggaaccgtaaaaaggccgcgttgctggcgtttttcc
45  ataggctccgcccccctgacgagcatcacaaaaatcgacgctcaagtcagaggtggcgaaacccgacaggactataaagataccaggcgtttccc
    cctggaagctccctcgtgcgctctcctgttccgaccctgccgcttaccggatacctgtccgcctttctcccttcgggaagcgtggcgctttctcatagct

FIGURE 5 (CONT.)

```
     cacgctgtaggtatctcagttcggtgtaggtcgttcgctccaagctgggctgtgtgcacgaaccccccgttcagcccgaccgctgcgccttatccggt
     aactatcgtcttgagtccaacccggtaagacacgacttatcgccactggcagcagccactggtaacaggattagcagagc
 5   gaggtatgtaggcggtgctacagagttcttgaagtggtggcctaactacggctacactagaaggacagtatttggtatctgcgctctgctgaagccag
     ttaccttcggaaaaagagttggtagctcttgatccggcaaacaaaccaccgctggtagcggtggttttttgtttgcaagcagcagattacgcgcagaa
     aaaaaggatctcaagaagatcctttgatcttttctacggggtctgacgctcagtggaacgaaaactcacgttaagggattttggtcatgagattatcaaa
     aaggatcttcacctagatcctttaaattaaaaatgaagttttaaatcaatctaaagtatatatgagtaaacttggtctgacagttaccaatgcttaatcagt
     gaggcacctatctcagcgatctgtctatttcgttcatccatagttgcctgactccccgtcgtgtagataactacgatacgggagggcttaccatctggcc
10   ccagtgctgcaatgataccgcgagacccacgctcaccggctccagatttatcagcaataaaccagccagccggaagggccgagcgcagaagtgg
     tcctgcaactttatccgcctccatccagtctattaattgttgccgggaagctagagtaagtagttcgccagttaatagtttgcgcaacgttgttgccattgc
     tacaggcatcgtggtgtcacgctcgtcgtttggtatggcttcattcagctccggttcccaacgatcaaggcgagttacatgatcccccatgttgtgcaaa
     aaagcggttagctccttcggtcctccgatcgttgtcagaagtaagttggccgcagtgttatcactcatggttatggcagcactgcataattctcttactgt
     catgccatccgtaagatgcttttctgtgactggtgagtactcaaccaagtcattctgagaatagtgtatgcggcgaccgagttgctcttgcccggcgtca
15   atacgggataataccgcgccacatagcagaactttaaaagtgctcatcattggaaaacgttcttcggggcgaaaactctcaaggatcttaccgctgttg
     agatccagttcgatgtaacccactcgtgcacccaactgatcttcagcatcttttactttcaccagcgtttctgggtgagcaaaaacaggaaggcaaaat
     gccgcaaaaaagggaataagggcgacacggaaatgttgaatactcatactcttccttttcaatattattgaagcatttatcagggttattgtctcatgag
     cggatacatatttgaatgtatttagaaaaataaacaaataggggttccgcgcacatttccccgaaaagtgccacctgacgtctaagaaaccattattatc
     atgacattaacctataaaaataggcgtatcacgaggccctttcgtctcgcgcgtttcggtgatgacggtgaaaacctctgacacatgcagctcccgga
20   gacggtcacagcttgtctgtaagcggatgccgggagcagacaagcccgtcagggcgcgtcagcgggtgttggcgggtgtcggggctggcttaact
     atgcggcatcagagcagattgtactgagagtgcaccatatgcggtgtgaaataccgcacagatgcgtaaggagaaaataccgcatcaggcgccatt
     cgccattcaggctgcgcaactgttgggaagggcgatcggtgcgggcctcttcgctattacgccagctggcgaaaggggggatgtgctgcaaggcga
     ttaagttgggtaacgccagggttttcccagtcacgacgttgtaaaacgacggcgcaaggaatggtgcatgcaaggagatggcgcccaacagtcccc
     cggccacggggcctgccaccatacccacgccgaaacaagcgctcatgagcccgaagtggcgagcccgatcttccccatcggtgatgtcggcgat
25   ataggcgccagcaaccgcacctgtggcgccggtgatgccggccacgatgcgtccggcgtagaggcgattagtccaatttgttaaagacaggatatc
     agtggtccaggctctagttttgactcaacaatatcaccagctgaagcctatagagtacgagccatagataaaataaaagattttatttagtctccagaaa
     aagggggaa
```

RETROVIRAL VECTORS FOR DELIVERY OF INTERFERING RNA

FIELD OF THE INVENTION

The present invention relates generally to retroviral vectors for delivering interfering RNA into a cell.

BACKGROUND OF THE INVENTION

RNA interference (RNAi) describes a phenomenon in which the presence of double-stranded RNA (dsRNA) having a sequence that is identical or highly similar to a portion of a target gene results in the degradation of messenger RNA (mRNA) transcribed from that targeted gene (Sharp 2001). Fjose et al. have proposed a mechanism for RNA interference [Fjose et al. RNA Interference: Mechanisms and Applications. Biotechnology Annual Review, Vol. 7, pp. 10-57 (2001)]. Initially a double stranded RNA sequence (dsRNA) sequence is made available with one strand that is identical or highly similar to a target gene and complementary to an mRNA produced from the transcription of the target gene (the sense strand), and an antisense strand that is complementary to the sense strand. Thus, the antisense sense strand has an identical or highly similar sequence to a portion of the mRNA that results from the transcription of the target gene.

An RNAi nuclease then cleaves the dsRNA into short double stranded fragments whose lengths may vary from 18-25 nucleotides, and binds to the mRNA produced from the transcription of the target gene. An RNAi enzyme having helicase activity then catalyzes an exchange between the short dsRNA and the mRNA so that the antisense strand of the dsRNA anneals to the mRNA, replaces the "antisense" strand of the dsRNA, and the mRNA is cleaved at its ends. Consequently, the mRNA is destroyed, and translation of the mRNA molecule does not occur. Moreover, the sense strand of the short dsRNA, which remains bound to the RNAi nuclease, serves as a template for production of a new antisense strand, forming a new dsRNA molecule for use in the destruction of another mRNA produced from the transcription of the target gene. Thus, RNAi demonstrates a catalytic activity. (Id.)

The ability to specifically knock-down expression of a target gene by RNAi has obvious benefits. For example, RNAi may be used to generate animals that mimic true genetic "knockout" animals to study gene function. In addition, RNAi may be useful in treating diseases or disorders that arise from the abnormal expression of a particular gene or group of genes, or the expression of a gene having a particular mutation or polymorphism. For example, genes contributing to a cancerous state (e.g., oncogenes) may be inhibited. In addition, viral genes may be inhibited, as well as mutant genes causing genetic diseases such as myotonic dystrophy, cystic fibrosis, Alzheimer's Disease, Parkinson's Disease, etc. Inhibiting such genes as cyclooxygenase or cytokines may also have applications in treating inflammatory diseases such as arthritis.

Accordingly, what is needed is a vehicle that delivers heterologous RNA into a cell in order to utilize interference RNA to modulate, and particularly, to down-regulate the expression of a particular target gene within a cell.

The citation of any reference herein should not be construed as an admission that such reference is available as "Prior Art" to the instant application.

SUMMARY OF THE INVENTION

Provided herein is a useful and heretofore unknown retroviral viral vector that permits the delivery of heterologous RNA into a cell in order to utilize RNA interference to modulate the expression of a particular protein.

Broadly, the present invention extends to a retroviral vector for carrying a target gene specific insert into a cell in order to modulate the expression of a target gene. Such a retroviral vector of the present invention comprises a promoter, a polylinker region, and a target gene specific insert comprising double stranded RNA, which comprises a sense portion that is complementary to a portion of the antisense strand of the target gene, and an antisense portion that is complementary to the sense portion. Thus, the sense and antisense portions of the double stranded RNA anneal, and the double stranded RNA folds back upon itself.

Numerous promoters have applications in a retroviral vector of the present invention. A particular example having applications in a retroviral vector of the present invention is the U6 promoter sequence of:

```
                                                (SEQ ID NO:7)
ttcccatgattccttcatatttgcatatacgatacaaggctgttagagag ataattagaattaatttgactgtaaacacaaagatattagtacaaaatac gtgacgtagaaagtaataatttcttgggtagtttgcagtttttaaaatta tgttttaaaatggactatcatatgcttaccgtaacttgaaagtatttcga tttcttgcctttatatatcttgtggaaaggacgaaacaccg.
```

Another promoter region having applications in a retroviral vector of the present invention is the H1 promoter, which has a nucleotide sequence of:

```
                                                (SEQ ID NO:14)
-1 ccctttctcaccagagtatgtcttgaatattctaagggtttaggttt ctgtaaagtgcaaataccactaaagggtcttgtgtatcgctgtacgttta taa-100.
```

Likewise, numerous polylinker regions readily have applications in a retroviral vector of the present invention. Examples of polylinker regions having applications in a retroviral vector of the present invention are

```
(a) aattc gactggcacagcctccagg ttcaagaga cctggaggctgtgccagtc ttttt ggaa a    (SEQ ID NO:1)

(b) aattc gctgggactcctttgcatg ttcaagaga catgcaaaggagtcccagc ttttt ggaa a;   (SEQ ID NO:2)

(c) gatcc gactggcacagcctccagg ttcaagaga cctggaggctgtgccagtc ttttt ggaa a;   (SEQ ID NO:3)

(d) gatcc gctgggactcctttgcatg ttcaagaga catgcaaaggagtcccagc ttttt ggaa a    (SEQ ID NO:4)

(e) aattc gactccagtggtaatctac ttcaagaga gtagattaccactggagtc ttttt ggaa a;   (SEQ ID NO:5)
and (f) gatcc gactccagtggtaatctac ttcaagaga gtagattaccactggagtc ttttt ggaa a.   (SEQ ID NO:6)
```

For a Lentivirus retroviral vector of the present invention, the polylinker sequence can include an AgeI restriction site and an EcoRI restriction site so that a target gene insert such as set forth below can be inserted:

```
AgeI +1        Loop       Term  EcoRI
CCGGT G  (20 more bases) TTCAAGAGA (21 bases) TTTTT GGAA G A C  (20 more bases) AAGTTCTCT (21 bases) AAAAA CCTT CTTAA
(SEQ ID NOS: 15 and 16, respectively).
```

This insert contains AgeI and EcoRI restriction sites. The "20 or more bases" can be either the antisense or sense strand of the double stranded nucleotide sequence of the target gene insert. Naturally the "21 bases" also can either the antisense or sense strand. However, it is critical that both of these strands are complementary and anneal so that the double stranded RNA folds back upon itself. Moreover, the 9mer loop described above is only an example. Other loops having other sizes readily can be used in the present invention.

Furthermore, in a retroviral vector of the present invention, the length of the sense and antisense portions of the double stranded RNA in the target gene specific insert can vary. For example, the length of these portions can be 19-30 nucleotides, in particular, 19-25 nucleotides, and more particularly, 19-23 nucleotides, respectively.

Naturally, numerous genes can be the target gene for a retroviral vector of the present invention. Particular examples of a target gene can be a gene associated with a particular disease or disorder, e.g., an oncogene such as p53 or Mat8. A target gene can also be a gene associated with a neurodegenerative disease or disorder, such as, for example, a mutated amyloid precursor protein or a presenilin gene that is associated with Alzheimer's disease. A target gene can also be a gene that encodes an ion channel protein, a hormone, etc. Indeed, any gene for which it is desirous to interrupt its expression has applications as a target gene for a retroviral vector of the present invention. In a particular example described infra, the target gene is p38.

Numerous retroviruses have applications in a retroviral vector of the present invention. For example, a retroviral vector of the present invention may be constructed from a retrovirus such as HIV, MoMuLV ("murine Moloney leukaemia virus"), MSV ("murine Moloney sarcoma virus"), HaSV ("Harvey sarcoma virus"); SNV ("spleen necrosis virus"); RSV ("Rous sarcoma virus"), Friend virus, a murine stem cell virus (MSCV), a lentivirus, or even a defective retroviral vector such as that disclosed in WO95/02697, to name only a few. A particular retrovirus having applications herein is a Murine Stem Cell Virus (MSCV). Another particular retrovirus having applications herein is a modified Lentivirus wherein (a) the endogenous CMV promoter has been removed; and (b) a REV element that binds to a REV response element (RRE) is inserted into the virus.

Moreover, a retroviral vector of the present invention may further comprise a reporter gene, such as hrGFP, Blasti, Hygro, Puro, eGFP-Puro fusion etc.

In another embodiment, the present invention extends to a cell infected with a retroviral vector of the present invention. Such an infection can occur in vitro, in vivo, or ex vivo.

The present invention further extends to a modified Lentivirus vector for carrying double stranded RNA into a cell in order to modify the expression of a target gene, wherein:

(a) the endogenous CMV promoter of the Lentivirus has been removed, the modified Lentivirus vector comprising:

(i) a REV element that binds to a REV response element (RRE) is inserted;

(ii) a U6 promoter sequence of

```
                                              (SEQ ID NO:7)
ttcccatgattccttcatatttgcatatacgatacaaggctgttagagag ataattagaattaatttgactgtaaacacaaagatattagtacaaaatac gtgacgtagaaagtaataatttcttgggtagtttgcagtttttaaaatta tgttttaaaatggactatcatatgcttaccgtaacttgaaagtatttcga tttcttgcctttatatatcttgtggaaaggacgaaacaccg;
```
and (iii) a polylinker region;

(iv) a target gene insert that comprises said double stranded RNA, wherein the double stranded RNA comprises a sense portion that is complementary a portion of the antisense strand of the target gene, and an antisense portion that is complementary to the sense portion so that the sense portion and antisense portion anneal, and the double stranded RNA folds back upon itself.

Numerous polylinker regions have applications in a modified Lentivirus vector of the present invention. Particular examples include, but certainly are not limited to:

```
(a)  aattc gactggcacagcctccagg ttcaagaga cctggaggctgtgccagtc ttttt ggaa a    (SEQ ID NO:1)

(b)  aattc gctgggactcctttgcatg ttcaagaga catgcaaaggagtcccagc ttttt ggaa a;   (SEQ ID NO:2)

(c)  gatcc gactggcacagcctccagg ttcaagaga cctggaggctgtgccagtc ttttt ggaa a;   (SEQ ID NO:3)

(d)  gatcc gctgggactcctttgcatg ttcaagaga catgcaaaggagtcccagc ttttt ggaa a    (SEQ ID NO:4)

(e)  aattc gactccagtggtaatctac ttcaagaga gtagattaccactggagtc ttttt ggaa a;   (SEQ ID NO:5)
and (f)  gatcc gactccagtggtaatctac ttcaagaga gtagattaccactggagtc ttttt ggaa a,   (SEQ ID NO:6)
``` to name only a few.

In a modified Lentivirus retroviral vector of the present invention, the polylinker sequence can include an AgeI restriction site and an EcoRI restriction site so that a target gene insert such as set forth below can be inserted:

```
AgeI +1                    Loop            Term       EcoRI
CCGGT G (20 more bases) TTCAAGAGA (21 bases) TTTTT GGAA G A C (20 more bases) AAGTTCTCT (21 bases) AAAAA CCTT CTTAA
```

This insert contains AgeI and EcoRI restriction sites. The "20 or more bases" can be either the antisense or sense strand of the double stranded nucleotide sequence of the target gene insert. Naturally the "21 bases" also can either the antisense or sense strand. However, it is critical that both of these strands are complementary and anneal so that the double stranded RNA folds back upon itself. Moreover, the 9mer loop described above is only an example. Other loops having other sizes readily can be used in the present invention.

Furthermore, a modified Lentivirus of the present invention may optionally include a reporter gene, such as Blasti, hrGFP luciferase, etc.

Particular examples of a modified Lentivirus of the present invention described herein are (a) pLenti-U6-Blasti, which comprises the nucleotide sequence of SEQ ID NO:8 (FIG. 1); and (b) pLenti-U6-hrGFP, which comprises the nucleotide sequence of SEQ ID NO:9 (FIG. 2).

For a Lentivirus retroviral vector of the present invention, the polylinker sequence can include an AgeI restriction site and an EcoRI restriction site so that a target gene insert such as set forth below can be inserted:

```
AgeI +1         Loop      Term    EcoRI
CCGGT G (20 more bases) TTCAAGAGA (21 bases) TTTTT GGAA G A C (20 more bases) AAGTTCTCT (21 bases) AAAAA CCTT CTTAA
(SEQ ID NOS: 15 and 16, respectively).
```

The present invention also extends to a Murine Stem Cell Virus (MSCV) vector for carrying double stranded RNA into a cell in order to modify the expression of a target gene, comprising:

(a) a promoter; and
(b) a polylinker region,
(c) a target gene insert comprising the double stranded RNA, which in turn comprises a sense portion that is complementary a portion of the antisense strand of the target gene, and an antisense portion that is complementary to the sense portion so that the sense portion and antisense portion anneal, and the double stranded RNA folds back upon itself.

Various promoter sequences can be used in an MSCV retroviral vector of the present invention. A particular example of such a promoter sequence is the U6 promoter sequence of

```
                                                    (SEQ ID NO:7)
ttcccatgattccttcatatttgcatatacgatacaaggctgttagagag ataattagaattaatttgactgtaaacacaaagatattagtacaaaatac gtgacgtagaaagtaataatttcttgggtagtttgcagtttttaaaatta tgttttaaaatggactatcatatgcttaccgtaacttgaaagtatttcga tttcttgcctttatatatcttgtggaaaggacgaaacaccg.
```

Another promoter having applications herein is the H1 promoter (SEQ ID NO: 14).

Furthermore, numerous polylinker regions have applications in a MSCV retroviral vector of the present invention. Particular examples include, but certainly are not limited to:

```
(a) aattc gactggcacagcctccagg ttcaagaga cctggaggctgtgccagtc ttttt ggaa a    (SEQ ID NO:1)

(b) aattc gctgggactcctttgcatg ttcaagaga catgcaaaggagtcccagc ttttt ggaa a;   (SEQ ID NO:2)

(c) gatcc gactggcacagcctccagg ttcaagaga cctggaggctgtgccagtc ttttt ggaa a;   (SEQ ID NO:3)

(d) gatcc gctgggactcctttgcatg ttcaagaga catgcaaaggagtcccagc ttttt ggaa a    (SEQ ID NO:4)

(e) aattc gactccagtggtaatctac ttcaagaga gtagattaccactggagtc ttttt ggaa a;   (SEQ ID NO:5)
and (f) gatcc gactccagtggtaatctac ttcaagaga gtagattaccactggagtc ttttt ggaa a,   (SEQ ID NO:6)
```

Optionally, a MSCV retroviral vector of the present invention can also comprise a reporter gene, such as Hygro, Puro, hrGFP, luciferase, or eGFP-Puro fusion.

Particular examples of MSCV retroviral vectors of the present invention include (a) MSCV-U6-Hygro, which comprises the nucleotide sequence of SEQ ID NO:10 (FIG. 3);

(b) MSCV-U6-Puro, which comprises the nucleotide sequence of SEQ ID NO:11 (FIG. 4); and (c) MSCV-U6-hrGFP, which comprises the nucleotide sequence of SEQ ID NO:12 (FIG. 5), to name only a few.

Accordingly, it is an aspect of the present invention to provide a retroviral vector having a gene target insert that folds back upon itself to form a duplex, wherein one strand of the duplex is a sense strand and the other strand of the duplex is an antisense strand. When the retroviral vector is processed in the cell, the duplex is cleaved from the vector to form a short dsRNA for use as interfering RNA in modulating the expression of the target gene.

It is another aspect of the present invention to provide a retroviral vector in which the sense strand of the target gene insert is identical or highly similar to a target gene that is associated with a particular disease or disorder. Such a retroviral vector may readily have applications in treating the disease or disorder associated with the expression of the target gene.

It is another aspect of the present invention to provide a cell that has been infected with a retroviral vector of the present invention. Such infection may occur in vitro, in vivo, or ex vivo. As a result of this infection, the expression of the target gene with the cell's genome is modulated, and in particular, decreased.

It is still another aspect of the present invention to provide a method for modulating the expression of a target gene in cell using interfering RNA, wherein the cell is infected with a retroviral vector of the present invention comprising a target gene insert having a sense strand that is identical or highly similar to the target gene.

These and other aspects of the present invention will be better appreciated by reference to the following drawings and Detailed Description.

BRIEF DESCRIPTION OF THE DRAWINGS

FIG. 1: Nucleotide sequence of modified Lentivirus vector pLenti-U6-Blasti of the present invention containing the Blasti reporter gene and the U6 promoter sequence. A target gene insert for modulating a particular gene can readily be inserted into the polylinker of this vector prior to infection of a cell with the vector.

FIG. 2: Nucleotide sequence of modified Lentivirus vector pLenti-U6-hrGFP of the present invention containing the hrGFP reporter gene and the U6 promoter sequence. A target gene insert for modulating a particular gene can readily be inserted into the polylinker of this vector prior to infection of a cell with the vector.

FIG. 3: Nucleotide sequence of MSCV vector MSCV-U6-Hygro of the present invention containing the Hygro reporter gene and the U6 promoter sequence. A target gene insert for modulating a particular gene can readily be inserted into the polylinker of this vector prior to infection of a cell with the vector.

FIG. 4: Nucleotide sequence of MSCV vector MSCV-U6-Hygro of the present invention containing the Hygro reporter gene and the U6 promoter sequence. A target gene insert for modulating a particular gene can readily be inserted into the polylinker of this vector prior to infection of a cell with the vector.

FIG. 5: Nucleotide sequence of MSCV vector MSCV-U6-hrGFP of the present invention containing the hrGFP reporter gene and the U6 promoter sequence. A target gene insert for modulating a particular gene can readily be inserted into the polylinker of this vector prior to infection of a cell with the vector.

DETAILED DESCRIPTION OF THE INVENTION

Figure 6:
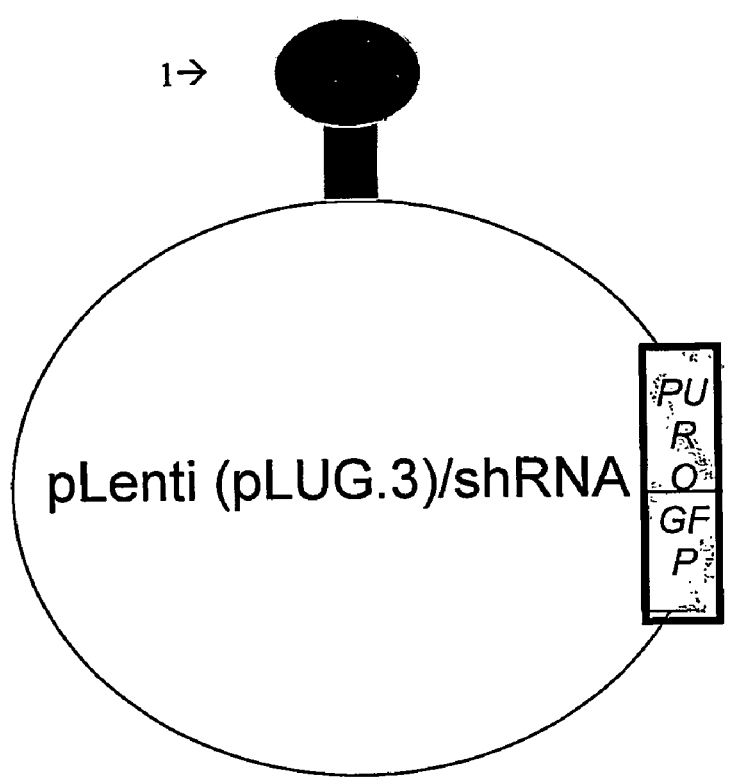
FIG. 6: a schematical view of a modified Lentivirus of the present invention that comprises a GFP reporter gene. (1) is the target gene insert, i.e., the double stranded RNA that folds back upon itself.

As explained the above, the present invention broadly extends to a useful and heretofore unknown retroviral vector having applications in delivering interfering RNA into a cell to modulate, and more particularly to down-regulate the expression of a particular target gene. Such a retroviral vector of the present invention comprises:

(a) a promoter, (b) a polylinker region, and (c) a target gene specific insert that comprises double stranded RNA, wherein the double stranded RNA comprises a sense portion that is complementary a portion of the antisense strand of the target gene, and an antisense portion that is complementary to the sense portion, so that the sense portion and antisense portion anneal, and the double stranded RNA folds back upon itself.

In a cell, the target gene specific insert that folds back upon itself is processed into a short dsRNA duplex, of which the sense strand can be used as interfering RNA. This interfering RNA modulates, and more particularly, down-regulates the expression the target gene. Surprisingly and unexpectedly, a retroviral vector of the present invention that is used to infect a cell can down-regulate gene expression of the target gene for the life of the cell, as opposed to the mere insertion of naked siRNA into the cell, which has been found to typically down-regulate the expression of the target gene for only 5-6 days.

Since a retroviral vector of the present invention is able to down-regulate the expression of the target gene, the retroviral vector may have applications in treating a wide variety of diseases or disorders related to the expression of a particular target, or related to the expression of a particular target gene that contains a mutation or polymorphism.

In accordance with the present invention there may be employed conventional molecular biology, microbiology, and recombinant nucleic acid molecule techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is an agent, such as plasmid, phage, virus or cosmid, used to transmit genetic material to a cell or organism.

"Heterologous" nucleic acid molecule refers to a nucleic acid molecule not naturally located in the cell, or in a chromosomal site of the cell.

A "nucleic acid molecule" or a "nucleotide sequence" can be used interchangeably, and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acid molecules, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acid molecules contain complementary sequences, although depending on the stringency of the hybridization, mismatches between bases are possible. The appropriate stringency for hybridizing nucleic acid molecules depends on the length of the nucleic acid molecules and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acid molecules, i.e., oligonucleotides, the position of mismatches becomes more important, and the length of the oligonucleotide determines its specificity (see Sambrook et al., supra, 11.7-11.8). A minimum length for a hybridizable nucleic acid molecule is at least about 15 nucleotides; in particular at least about 40 nucleotides; more particularly the length is at least about 30 nucleotides; more particularly at least about 60 nucleotides, and even more particularly at least 100 nucleotides.

Furthermore, as used herein, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A nucleic acid molecule "coding sequence" or "sense strand" is a nucleic acid molecule or portion thereof for eukaryotic genomic DNA molecules, which encodes a polypeptide or portion thereof with codons of the genetic code in a correct reading frame. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |

-continued

| | |
|---|---|
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

As used herein, the term "portion" with respect to a nucleotide sequence refers to a part of said sequence having a length of at least 19 contiguous nucleotides, but less than the entire nucleotide sequence.

A "promoter sequence" or "promoter" is a nucleic acid molecule regulatory region capable of binding RNA polymerase in a cell and initiating transcription of a downstream (3' direction) coding sequence. Within the promoter sequence will be found a transcription initiation site (conveniently defined for example, by mapping with nuclease SI), as well as protein binding domains (consensus sequences) responsible for the binding of RNA polymerase. A particular promoter sequence having applications in the present invention includes the U6 promoter sequence, which has the nucleotide sequence of:

(SEQ ID NO:7)
ttcccatgattccttcatatttgcatatacgatacaaggctgttagagag ataattagaattaatttgactgtaaacacaaagatattagtacaaaatac gtgacgtagaaagtaataatttcttgggtagtttgcagttttttaaaatta tgttttaaaatggactatcatatgcttaccgtaacttgaaagtatttcga tttcttgcctttatatatcttgtggaaaggacgaaacaccg.

Another example of promoter sequence having applications in a vector of the present invention is the H1 promoter (SEQ ID NO: 14).

As used herein, the terms "polylinker" or "polylinker region" can be used interchangeably, and refer to a nucleotide sequence that is inserted into a retroviral vector of the present invention and contains a plurality of restriction sites for particular restriction enzymes. Thus, using the particular restriction enzymes a nucleotide sequence can be inserted into a vector of the present invention. Particular examples of polylinkers having applications in a vector of the present invention include, but certainly are not limited to:

```
(a)  aattc gactggcacagcctccagg ttcaagaga cctggaggctgtgccagtc ttttt ggaa a   (SEQ ID NO:1)

(b)  aattc gctgggactcctttgcatg ttcaagaga catgcaaaggagtcccagc ttttt ggaa a;  (SEQ ID NO:2)

(c)  gatcc gactggcacagcctccagg ttcaagaga cctggaggctgtgccagtc ttttt ggaa a;  (SEQ ID NO:3)

(d)  gatcc gctgggactcctttgcatg ttcaagaga catgcaaaggagtcccagc ttttt ggaa a   (SEQ ID NO:4)

(e)  aattc gactccagtggtaatctac ttcaagaga gtagattaccactggagtc ttttt ggaa a;  (SEQ ID NO:5)
and (f)  gatcc gactccagtggtaatctac ttcaagaga gtagattaccactggagtc ttttt ggaa a.  (SEQ ID NO:6)
```

In a particular embodiment of the present invention, e.g. a modified Lentivirus retroviral vector, the polylinker sequence can include an AgeI restriction site and an EcoRI restriction site so that a target gene insert such as set forth below can be inserted:

```
AgeI +1                        Loop             Term    EcoRI
CCGGT G (20 more bases) TTCAAGAGA (21 bases) TTTTT GGAA G A C (20 more bases) AAGTTCTCT (21 bases) AAAAA CCTT CTTAA
```

This insert contains AgeI and EcoRI restriction sites. The "20 or more bases" can be either the antisense or sense strand of the double stranded nucleotide sequence of the target gene insert. Naturally the "21 bases" also can either the antisense or sense strand. However, it is critical that both of these strands are complementary and anneal so that the double stranded RNA folds back upon itself. Moreover, the 9mer loop described above is only an example. Other loops having other sizes readily can be used in the present invention.

As used herein, the term "infect" refers to the contamination of a cell with a retroviral vector of the present invention, wherein the cell possesses the gene target within its genome. Thus, infecting the cell with a retroviral vector of the present invention with the proper target gene insert will result in modulating the expression of the target gene in the infected cell.

As used herein, the term "modulate" or "modulating" refers to altering the normal expression of a target gene in an infected cell. In particular, these terms refer to decreasing the amount expression of the target gene in the infected cell as compared to the amount of expression of the target gene measured in the cell prior to infection with a retroviral vector of the present invention, or a decrease in the amount of expression of the target gene in the infected cell as compared to the expression of the target gene in an uninfected control cell.

Retroviral Vectors

As explained above, the present invention extends to a retroviral vector for carrying a target gene specific insert into a cell in order to modify the expression of a target gene, comprising:
(a) a promoter;
(b) a polylinker region;
(c) a target gene specific insert comprising double stranded RNA, wherein the double stranded RNA comprises a sense portion that is complementary a portion of the antisense strand of the target gene, and an antisense portion that is complementary to the sense portion, so that the sense portion and antisense portion anneal, and the double stranded RNA folds back upon itself.

Retroviruses are integrating viruses that infect dividing cells. The retrovirus genome includes two LTRs, an encapsulation sequence and three coding regions (gag, pol and env). Particular examples of retroviruses having applications herein, include, but certainly are not limited to retrovirus such as HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus"), a Friend virus, and a defective retroviral vector such as one disclosed in WO95/02697, which hereby incorporated by reference herein in its entirety.

In general, in order to construct a recombinant retrovirus containing a nucleic acid sequence, a plasmid is constructed which contains the nucleic acid sequence, which in the case of the present invention, is an RNA sequence that comprises a target gene specific insert as described above, and a polylinker region. Optionally, the RNA sequence can also comprise a nucleic acid that encodes a reporter protein. This construct is then used to transfect a packaging cell line, which cell line is able to supply in trans the retroviral functions, which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). After the construction, a retroviral vector of the present invention can be purified by standard techniques known to those having ordinary skill in the arL A detailed description of the construction of a retroviral vector of the present invention is set forth infra.

A particular type of retrovirus having applications in a retroviral vector of the present invention is a modified Lentivirus, which is able to infect post mitotic cells and/or non-dividing cells. Such types of cells can be found in liver and muscle neurons. In a modified Lentivirus vector of the present invention, the endogenous CMV promoter of a Lentivirus is removed, and a REV element is inserted into the virus.

Anther type of retrovirus having applications in a retroviral vector of the present invention is the MSCV virus.

Administration of a Retroviral Vector of the Invention Via Infection, Transfection or Transformation The present invention further extends to a cell infected with a retroviral vector of the present invention, wherein the infected cell contains the target gene within its genome. Hence, the infection of the cell with a retroviral vector of the present invention can modulate, and particularly, decrease the expression of the target gene within the cell. Such infection can occur in vivo, in vitro, or ex vivo. Numerous types of cells can be infected with a retroviral vector of the present invention. For example, such a cell can be a prokaryotic or eukaryotic cell, e.g., bacterial cells such as *E. coli*, yeast cells or mammalian cells. Furthermore, such cells can be obtained from a biological sample such as, e.g., hair or skin, or body fluids, e.g., blood, saliva or semen, etc. However, as explained above, it is important that the cell contain the target gene within its genome.

Optionally, a cell can also be transformed or transfected with a retroviral vector of the present invention using routine laboratory techniques, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

For a Lentivirus retroviral vector of the present invention, the polylinker sequence can include an AgeI restriction site and an EcoRI restriction site so that a target gene insert such as set forth below can be inserted:

```
AgeI +1       Loop       Term    EcoRI
CCGGT G  (20 more bases)  TTCAAGAGA  (21 bases)  TTTTT  GGAA  G A C  (20 more bases)  AAGTTCTCT  (21 bases)  AAAAA  CCTT  CTTAA
(SEQ ID NOS: 15 and 16, respectively).
```

Pharmaceutical Compositions Containing a Retroviral Vector of the Invention

The present invention also extends to a pharmaceutical composition comprising a retroviral vector of the present invention and a pharmaceutically acceptable carrier for the administration of a retroviral vector of the present invention. As used herein, the phrase "pharmaceutically acceptable" refers to molecular entities and compositions that are physiologically tolerable and do not typically produce an allergic or similar untoward reaction, such as gastric upset, dizziness and the like. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A pharmaceutical composition of the present invention may be for administration for injection, or for oral, pulmonary, nasal or other forms of administration, and may include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, and rate of in vivo release. See, e.g., Remington's Pharmaceutical Sciences, 18th Ed. (1990, Mack Publishing Co., Easton, Pa. 18042) pages 1435-1712, which are herein incorporated by reference. The compositions may be prepared in liquid form, or may be in dried powder, such as lyophilized form.

The present invention may be better understood by reference to the following non-limiting Example, which is provided as exemplary of the invention. The following Example is presented in order to more fully illustrate the preferred embodiments of the invention. It should in no way be construed, however, as limiting the broad scope of the invention.

Example

Cloning shRNA into Lentiviral Vector Called LUG

Initially, upper and lower strands of short hairpin nucleotide sequences (21 bases of sense strand, 9 bases of loop and 21 bases antisense) are obtained. They can be either produced or purchased from an oligo vender. The two strands are then in one well of a 96-well format.

Then, 50 pmol/ul of the strands are annealed, and 0.05 pmoles of the annealed strands are used to ligate. The oligos were such that the upper and lower strands were combined together in a single well of a 96-well plate. All processes were carried out in a 96-well High-Throughput format.

For the annealing reaction, 5 µl of the oligo mix was added to 45 µl of the annealing mix (40 µl water+5 µl NEB buffer 2). The mixture was annealed by heating to 98° C. for 2 minutes in a thermocycler and then cooled on the bench top for at least 2 hours. The annealed oligos were then diluted to 1:100 and 1 µl of the diluted annealed oligos, i.e., the double stranded DNA of the target gene insert, was ligated into the polylinker of the retroviral vector backbone (which was pre-cut with AgeI and EcoRI). Ligations were carried out overnight at 4° C. 2 µl of the ligation was used to transform 40 µl of SURE cells (Stratagene) and the transformations were plated on 12 well carbenicillin (50 µg/ml) grid plates. The following day, colonies were picked into Super Broth-carbenicillin (50 µg/ml) and sent to HTP sequencing. The cultures were then mini-prepped and sequenced. The sequences were analyzed and positives were maxi-prepped to provide DNA for virus production.

Producing Modified Lentivirus in 293FT Cells:

Transfection Procedure:

One day prior to transfection, trypsinize and count the 293FT cells, plating them at 5×10 6 cells per 10 cm plate. Plate cells in 10 ml of growth medium containing serum.

On the day of transfection, remove the culture medium from the 293FT cells and replace with 5 ml of growth medium containing serum (or Opti-MEM® I Medium containing serum). Antibiotics must not be included.

Prepare DNA-Lipofectamine Z 2000 complexes for each transfection sample by performing the following:

Dilute 9 µg of the optimized packaging mix and 3 µg of pLenti expression plasmid DNA (12 µg total) in 1.5 ml of Opti-MEM® I Medium without serum. Mix gently.

Mix Lipofectamine 2000 gently before use, then dilute 36 µl in 1.5 ml of Opti-MEM® I Medium without serum. Mix gently and incubate for 5 minutes at room temperature.

After the 5-minute incubation, combine the diluted DNA with the diluted Lipofectamine 2000. Mix gently.

Incubate for 20 minutes at room temperature to allow the DNA-Lipofectamine 2000 complexes to form. The solution may appear cloudy, but this will not impede the transfection.

4. Add the DNA-Lipofectamine 2000 complexes dropwise to each plate. Mix gently by rocking the plate back and forth. Incubate the cells overnight at 37° C. in a $CO_2$ incubator.

5. The next day, remove the medium containing the DNA-Lipofectamine 2000 complexes and replace with complete culture medium (i.e. D-MEM containing 10% FBS, 2 mM L-glutamine, 0.1 mM MEM Non-Essential Amino Acids, and 1% penicmin/streptomycin).

A skilled artisan should note that expression of the VSV G glycoprotein causes 293FT cells to fuse, resulting in the appearance of multinucleated syncitia. This morphological change is normal and does not affect production of the lentivirus. It should also be noted that in practicing the present invention, one is interacting with infectious materials.

6. Harvest virus-containing supernatants 48-72 hours post-transfection by removing medium to a 15 ml sterile, capped, conical tube. Minimal differences in viral yield are observed whether supernatants are collected 48 or 72 hours post-transfection.

7. Centrifuge at 3000 rpm for 15 minutes at +4° C. to pellet cell debris.

8. Perform filtration step, if desired

9. Pipette viral supernatants into cryovials in 1 ml aliquots. Store viral stocks at −80° C.

Producing MSCV in GP2-293 Cells:

Cell are maintained in a complete medium of DMEM supplemented with 10% FBS, 100 µg/ml streptomycin, 100 units/ml penicillin G.

Propagating Cells form Frozen Stocks:

1. Thaw vial in a 37° C. waterbath.
2. Transfer the cells to a tube containing 9 ml of pre-warmed complete medium.
3. Centrifuge in 1500 rpm for 5 minutes.
4. Remove supernatant.
5. Gently resuspend cells in 10 ml of complete medium and plate in a 10 cm poly-D-lysine coated plate.
6. Incubate cells at 37° C. with 5% C02 poly-D-lysine coated plates can be used for the first week to promote adherence after thawing. Subsequently, the cells may be cultured on regular plates.

Maintaining Packaging Cells

1. Aspirate medium, wash cells once with pre-warmed PBS.
2. Add 1 ml of trypsin-EDTA to the plate. Incubate for 30 sec-1 min.
3. Add 4 mls of complete medium to inhibit trypsin.
4. Resuspend the cells by pipetting up and down several times.
5. Transfer 1 ml of cells to a 10 cm plate containing 9 ml of complete medium.

The cells should be split 1:5 every 3 days when the cells are at 80% confluence. Moreover, cell should not be over trypsinized since as a result, the cells tend to become clumpy and will not plate down well. Also, never let the cells get over confluent as this affects their packaging ability, and cells after Transfer/Passage #40 should not be used as their titers are compromised.

Infection of GP2-293 Cells:

Day 1: (around 3 µm)

Plate 3 to $3.9 \times 10^6$ cells per 10 cm plate (use poly-D-lysine coated plates).

Day 2 (around 12 noon)

4 hours before the infection, re-feed the cells with 10 ml of fresh medium (minus antibiotics).

Infection Method 1 (Calcium Phosphate/HBS)

1. Use 12 µg of expression vector (PMK0.1) (DNA1) and 12 µg VSV-G plasmid (DNA2) per transfection per 10 cm plate.
2. In a tube add:
DNA 1 12 µg
DNA 2 12 µg A retroviral vector of the present invention can exist as a dsDNA vector so that it can be propagated, such as in a plasmid. However, when it is packaged, it is a retrovirus and infection leads to injection of the virus nucleoprotein core (consisting mostly of gag-derived proteins, RNA vector, and the reverse transcriptase protein). Reverse transcriptase converts the retroviral vector of the present invention back into DNA and allows for stable integration into the genome of a cell infected. Furthermore, the DNA vector integrated (or transiently transfected) serves as the template for RNA polymerase III which binds to U6 promoter and transcribes shRNA from shDNA cloned into the vector. Above DNA1 is DNA vector (to deliver shRNA) and DNA2 is packaging plasmid.

Water
2M $CaCl_2$ 62 µl
Total Vol. 500 µl

3. In a separate tube, dispense 500 µl of 2×HBS.
4. Add the 2×BS dropwise to the DNA/$CaCl_2$ mixture whilst vortexing.
5. Incubate at room temperature for 20 minutes.
6. Vortex the DNA/$CaCl_2$ mixture gently.
7. Add the mixture to the packaging cells dropwise with a pipette.
8. Rock the plate back and forth to evenly distribute the solution.
9. Incubate the cells at 37° C. with 5% $CO_2$.

Transfection Method 2 (Lipofectamine 2000)

1. Use 6 µg of expression vector (pMK0.1) and 6 µg VSV-G plasmid per transfection per 10 cm plate.
2. Add the DNA to a tube.
3. In a separate tube, pipette 72 µl of Lipofectamine 2000 into a 1.5 ml of serum-free medium (Optimem).
4. Mix gently. Incubate at room temperature for 5 minutes.
5. Add the Lipofecatamine/Optimem mixture to the DNA, mix gently.
6. Incubate at room temperature for 15 minutes.
7. Add the DNA/Lipo/Optimem mixture to the packaging cells dropwise with a pipette.
8. Rock the plate back and forth to evenly distribute the solution.
9. Incubate the cells at 37° C. with 5% $CO_2$.

Do not allow the transfection complex to sit on the cells for more than 16 hours.

Day 3: (am)

1. Aspirate the medium.
2. Gently wash the cells once pre-warmed PBS
3. Add 5 mls of complete medium per 10 cm plate in order to concentrate the viral supernatant.
4. Incubate the cells at 37° C. with 5% $CO_2$.

Day 4: (am)

1. Harvest the medium, filter thru a 0.45 micron syringe filter.
2. Aliquot the virus, store at −80° C.
3. Re-feed the cells with 5 mls of complete medium.

This is the "24 hour viral supe" Harvesting the virus from the packaging cell line after 24 hours is 24 hour viral supernatant.

Day 5: (am)

1. Harvest the medium, filter thru a 0.45 micron syringe filter.
2. Aliquot the virus, store at −80° C.
3. Discard the plates.

This is the "48 hour viral supe" Harvesting the virus from the packaging cell line after 48 hours is 48 hour viral supernatant.

For Ecotropic Viruses, package in EcoPack Packaging Cell Line. For AN Amphotropic Virus, package in AmphoPack Packaging Cell line. For a Polytropic Virus, package in GP2-293 Packaging Cells (co-transfect vector with VSV-G expression plasmid)

Results

Using the procedures set forth above to produce a retroviral vector of the present invention, and then infecting cells having the target gene in their genome with a retroviral vector of the present invention, expression of the target gene has been successfully decreased. In a particular, the target gene insert for p38 was used, and the sequence for this target insert is set forth below.

(SEQ ID NO:13)
CCGGTGCAGGAGTTGAACAAGACAATACCTGATTGTCTTGTTCAGCTCCT
GCTTTTTGGAAG.

Figure 7:
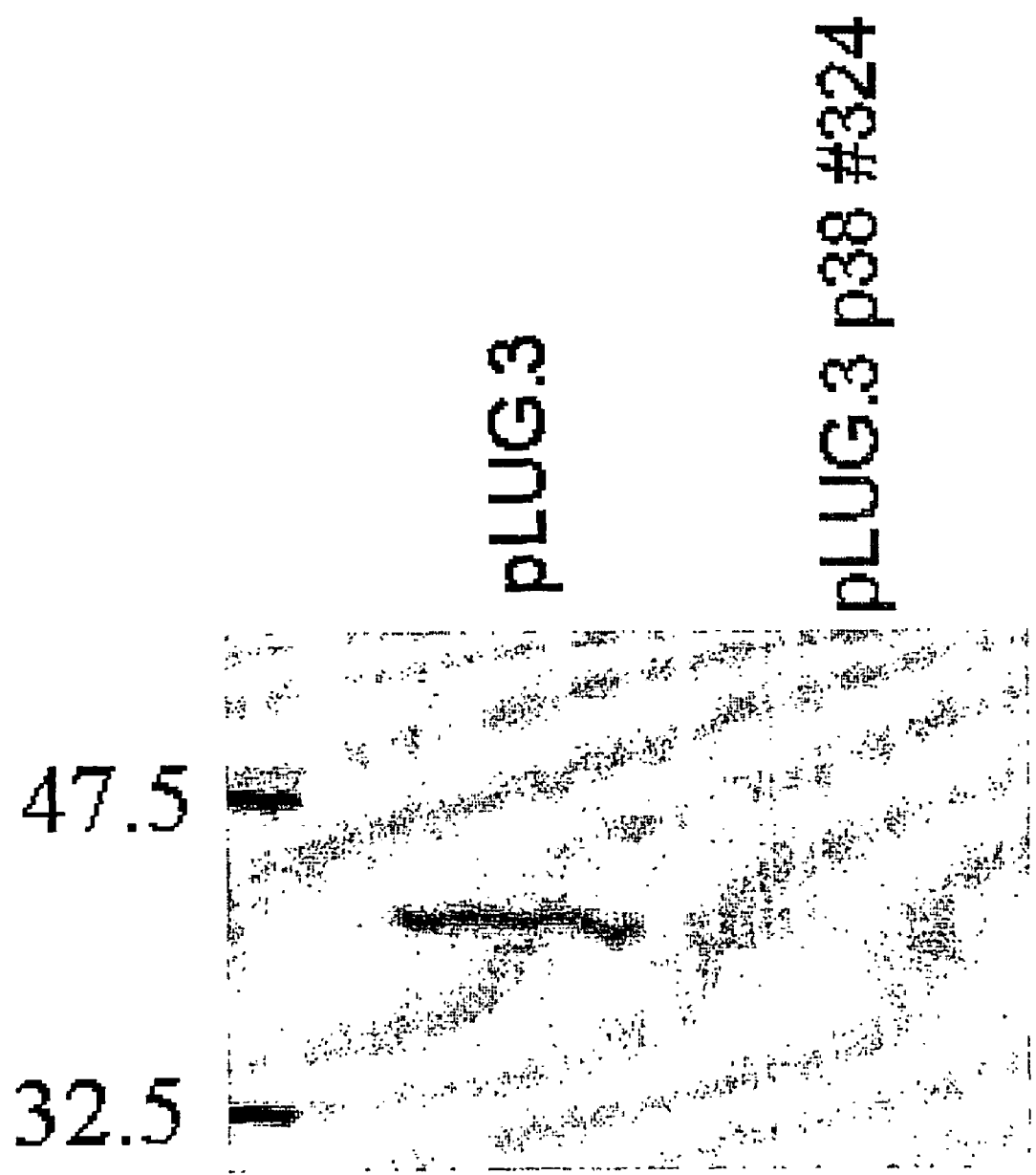
FIG. 7: a western blot comparing the expression of p38 in a cell infected with a modified Lentivirus of the present invention that lacks a target gene insert (a control) with the expression of p38 in a cell infected with a modified Lentivirus of the present invention having a target gene insert designed to be complementary to a portion of the cell's endogenous p38 gene. This blot clearly shows that the modified Lentivirus of the present invention decreased the expression of p38 relative to the expression in the control.

FIG. 7 clearly shows that a modified Lentivirus of the present invention having the target gene insert of double stranded RNA of SEQ ID NO:13, which was designed to interfere with expression of p38 in a cell, clearly decreased the expression of p38 in the cell relative to the expression of p38 in a control cell.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A retroviral vector for carrying a target gene specific insert into a cell in order to modify the expression of a target gene having a sense strand and an antisense strand, comprising:

(a) a U6 promoter having a sequence of:

```
                                              (SEQ ID NO:7)
ttcccatgattccttcatatttgcatatacgatacaaggctgttagagag ataattagaattaatttgactgtaaacacaaagatattagtacaaaatac gtgacgtagaaagtaataatttcttgggtagtttgcagttttaaaatta tgttttaaaatggactatcatatgcttaccgtaacttgaaagtatttcga tttcttgcctttatatatcttgtggaaaggacgaaacaccg;
and
```

(b) a polylinker region comprising a nucleotide sequence of gatcc gctgggactcctttgcatg ttcaagaga catgcaaaggagtcccagc ttttt ggaa a (SEQ ID NO:4)

(c) a target gene specific insert comprising double stranded RNA, wherein said double stranded RNA comprises a sense portion that is complementary to a portion of the antisense strand of the target gene, and an antisense portion that is complementary to the sense portion, so that the sense portion and antisense portion anneal, and the double stranded RNA folds back upon itself.

2. The retroviral vector of claim 1, wherein the sense and antisense regions of the target gene specific insert each comprise a length of 19-30 nucleotides.

3. The retroviral vector of claim 2, wherein the sense and antisense regions of the target gene specific insert each comprise a length of 19-25 nucleotides.

4. The retroviral vector of claim 3, wherein the sense and antisense regions of the target gene specific insert each comprise a length of 19-23 nucleotides.

5. A modified Lentivirus vector for carrying double stranded RNA into a cell in order to modify the expression of a target gene having a sense strand and an antisense strand, wherein:

(a) the endogenous CMV promoter of the Lentivirus has been removed, said modified Lentivirus vector comprising:

(i) a REV element that binds to a REV response element (RRE) is inserted;

(ii) a U6 promoter sequence of

```
                                              (SEQ ID NO:7)
ttcccatgattccttcatatttgcatatacgatacaaggctgttagagag ataattagaattaatttgactgtaaacacaaagatattagtacaaaatac gtgacgtagaaagtaataatttcttgggtagtttgcagttttaaaatta tgttttaaaatggactatcatatgcttaccgtaacttgaaagtatttcga tttcttgcctttatatatcttgtggaaaggacgaaacaccg; and
```

(b) a polylinker region comprising a nucleotide sequence of: gatcc gctgggactcctttgcatg ttcaagaga catgcaaaggagtcccagc ttttt ggaa a (SEQ ID NO:4);

wherein said double stranded RNA comprises a sense portion that is complementary to a portion of the antisense strand of the target gene, and an antisense portion that is complementary to the sense portion so that the sense portion and antisense portion anneal, and the double stranded RNA folds back upon itself.

6. The modified Lentivirus vector of claim 5, further comprising a reporter gene.

7. The modified Lentivirus vector of claim 5, wherein said reporter gene is selected from the group consisting of Blasti and hrGFP.

8. The modified Lentivirus vector of claim 7, wherein said vector is pLenti-U6-Blasti, which comprises the nucleotide sequence of SEQ ID NO:8.

9. A modified lentivirus pLenti-U6-Blasti, comprising the nucleotide sequence of SEQ ID NO:8.

10. A cell transformed or transfected with the modified lentivirus of claim 9.

* * * * *

UNITED STATES PATENT AND TRADEMARK OFFICE
CERTIFICATE OF CORRECTION

| | | |
|---|---|---|
| PATENT NO. | : 7,612,195 B2 | Page 1 of 1 |
| APPLICATION NO. | : 10/574416 | |
| DATED | : November 3, 2009 | |
| INVENTOR(S) | : Grueneberg et al. | |

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by 12 days.

Delete the phrase "by 12 days" and insert -- by 139 days --

Signed and Sealed this

Eighteenth Day of May, 2010

David J. Kappos
*Director of the United States Patent and Trademark Office*

SEQUENCE LISTING

```
<160> NUMBER OF SEQ ID NOS: 14

<210> SEQ ID NO 1
<211> LENGTH: 62
<212> TYPE: DNA
<213> ORGANISM: Artificial
<220> FEATURE:
<223> OTHER INFORMATION: Polylinker Sequence

<400> SEQUENCE: 1
aattcgactg gcacagcctc caggttcaag agacctggag gctgtgccag tcttttgga        60 aa                                                                      62

<210> SEQ ID NO 2
<211> LENGTH: 62
<212> TYPE: DNA
<213> ORGANISM: Artificial
<220> FEATURE:
<223> OTHER INFORMATION: Polylinker Sequence

<400> SEQUENCE: 2
aattcgctgg gactcctttg catgttcaag agacatgcaa aggagtccca gcttttgga        60 aa                                                                      62

<210> SEQ ID NO 3
<211> LENGTH: 62
<212> TYPE: DNA
<213> ORGANISM: Artificial
<220> FEATURE:
<223> OTHER INFORMATION: Polylinker Sequence

<400> SEQUENCE: 3
gatccgactg gcacagcctc caggttcaag agacctggag gctgtgccag tcttttgga        60 aa                                                                      62

<210> SEQ ID NO 4
```

<211> LENGTH: 62
<212> TYPE: DNA
<213> ORGANISM: Artificial
<220> FEATURE:
<223> OTHER INFORMATION: Polylinker Sequence

<400> SEQUENCE: 4

```
gatccgctgg gactcctttg catgttcaag agacatgcaa aggagtccca gcttttttgga    60
aa                                                                   62
```

<210> SEQ ID NO 5
<211> LENGTH: 62
<212> TYPE: DNA
<213> ORGANISM: Artificial
<220> FEATURE:
<223> OTHER INFORMATION: Polylinker sequence

<400> SEQUENCE: 5

```
aattcgactc cagtggtaat ctacttcaag agagtagatt accactggag tcttttttgga    60
aa                                                                   62
```

<210> SEQ ID NO 6
<211> LENGTH: 62
<212> TYPE: DNA
<213> ORGANISM: Artificial
<220> FEATURE:
<223> OTHER INFORMATION: Polylinker Sequence

<400> SEQUENCE: 6

```
gatccgactc cagtggtaat ctacttcaag agagtagatt accactggag tcttttttgga    60
aa                                                                   62
```

<210> SEQ ID NO 7
<211> LENGTH: 241
<212> TYPE: DNA
<213> ORGANISM: Artificial
<220> FEATURE:
<223> OTHER INFORMATION: U6 Promoter sequence

<400> SEQUENCE: 7

```
ttcccatgat tccttcatat ttgcatatac gatacaaggc tgttagagag ataattagaa    60
ttaatttgac tgtaaacaca agatattag tacaaaatac gtgacgtaga aagtaataat   120
ttcttgggta gtttgcagtt tttaaaatta tgttttaaaa tggactatca tatgcttacc   180
gtaacttgaa agtatttcga tttcttgcct ttatatatct tgtggaaagg acgaaacacc   240
g                                                                  241
```

<210> SEQ ID NO 8
<211> LENGTH: 6498
<212> TYPE: DNA
<213> ORGANISM: Artificial
<220> FEATURE:
<223> OTHER INFORMATION: Modified lentivirus (pLenti-U6-Blasti)

<400> SEQUENCE: 8

```
aatgtagtct tatgcaatac tcttgtagtc ttgcaacatg gtaacgatga gttagcaaca    60
tgccttacaa ggagagaaaa agcaccgtgc atgccgattg gtggaagtaa ggtggtacga   120
tcgtgcctta ttaggaaggc aacagacggg tctgacatgg attggacgaa ccactgaatt   180
gccgcattgc agagatattg tatttaagtg cctagctcga tacataaacg ggtctctctg   240
gttagaccag atctgagcct gggagctctc tggctaacta gggaacccac tgcttaagcc   300
```

-continued

| | |
|---|---|
| tcaataaagc ttgccttgag tgcttcaagt agtgtgtgcc cgtctgttgt gtgactctgg | 360 |
| taactagaga tccctcagac ccttttagtc agtgtggaaa atctctagca gtggcgcccg | 420 |
| aacagggact tgaaagcgaa agggaaacca gaggagctct ctcgacgcag gactcggctt | 480 |
| gctgaagcgc gcacggcaag aggcgagggg cggcgactgg tgagtacgcc aaaaattttg | 540 |
| actagcggag gctagaagga gagagatggg tgcgagagcg tcagtattaa gcgggggaga | 600 |
| attagatcgc gatgggaaaa aattcggtta aggccagggg gaaagaaaaa atataaatta | 660 |
| aaacatatag tatgggcaag cagggagcta gaacgattcg cagttaatcc tggcctgtta | 720 |
| gaaacatcag aaggctgtag acaaatactg ggacagctac aaccatccct tcagacagga | 780 |
| tcagaagaac ttagatcatt atataataca gtagcaaccc tctattgtgt gcatcaaagg | 840 |
| atagagataa aagacaccaa ggaagcttta dacaagatag aggaagagca aaacaaaagt | 900 |
| aagaccaccg cacagcaagc ggccgctgat cttcagacct ggaggaggag atatgaggga | 960 |
| caattggaga agtgaattat ataaatataa agtagtaaaa attgaaccat taggagtagc | 1020 |
| acccaccaag gcaaagagaa gagtggtgca gagagaaaaa agagcagtgg gaataggagc | 1080 |
| tttgttcctt gggttcttgg gagcagcagg aagcactatg ggcgcagcgt caatgacgct | 1140 |
| gacggtacag gccagacaat tattgtctgg tatagtgcag cagcagaaca atttgctgag | 1200 |
| ggctattgag gcgcaacagc atctgttgca actcacagtc tggggcatca agcagctcca | 1260 |
| ggcaagaatc ctggctgtgg aaagatacct aaaggatcaa cagctcctgg ggatttgggg | 1320 |
| ttgctctgga aaactcattt gcaccactgc tgtgccttgg aatgctagtt ggagtaataa | 1380 |
| atctctggaa cagatttgga atcacacgac ctggatggag tgggacagag aaattaacaa | 1440 |
| ttacacaagc ttaatacact ccttaattga agaatcgcaa aaccagcaag aaaagaatga | 1500 |
| acaagaatta ttggaattag ataaatgggc aagtttgtgg aattggttta acataacaaa | 1560 |
| ttggctgtgg tatataaaat tattcataat gatagtagga ggcttggtag gtttaagaat | 1620 |
| agttttgct gtactttcta tagtgaatag agttaggcag ggatattcac cattatcgtt | 1680 |
| tcagacccac ctcccaaccc cgaggggacc cgacaggccc gaaggaatag aagaagaagg | 1740 |
| tggagagaga gacagagaca gatccattcg attagtgaac ggatctcgac ggtaatcgat | 1800 |
| tttcccatga ttccttcata tttgcatata cgatacaagg ctgttagaga gataattaga | 1860 |
| attaatttga ctgtaaacac aaagatatta gtacaaaata cgtgacgtag aaagtaataa | 1920 |
| tttcttgggt agtttgcagt ttttaaaatt atgttttaaa atggactatc atatgcttac | 1980 |
| cgtaacttga aagtatttcg atttcttggc tttatatatc ttgtggaaag gacgaaacac | 2040 |
| cgaattcacc ggtcggttag taatgagttt ggaattaatt ctgtggaatg tgtgtcagtt | 2100 |
| agggtgtgga aagtccccag gctccccagg caggcagaag tatgcaaagc atgcatctca | 2160 |
| attagtcagc aaccaggtgt ggaaagtccc caggctcccc agcaggcaga agtatgcaaa | 2220 |
| gcatgcatct caattagtca gcaaccatag tcccgcccct aactccgccc atcccgcccc | 2280 |
| taactccgcc cagttccgcc cattctccgc cccatggctg actaattttt tttatttatg | 2340 |
| cagaggccga ggccgcctct gcctctgagc tattccagaa gtagtgagga ggcttttttg | 2400 |
| gaggcctagg cttttgcaaa aagctcccgg gagcttgtat atccattttc ggatctgatc | 2460 |
| agcacgtgtt gacaattaat catcggcata gtatatcggc atagtataat acgacaaggt | 2520 |
| gaggaactaa accatggcca agcctttgtc tcaagaagaa tccaccctca ttgaaagagc | 2580 |
| aacggctaca atcaacagca tccccatctc tgaagactac agcgtcgcca gcgcagctct | 2640 |

```
ctctagcgac ggccgcatct tcactggtgt caatgtatat cattttactg ggggaccttg    2700
tgcagaactc gtggtgctgg gcactgctgc tgctgcggca gctggcaacc tgacttgtat    2760
cgtcgcgatc ggaaatgaga acaggggcat cttgagcccc tgcggacggt gccgacaggt    2820
gcttctcgat ctgcatcctg ggatcaaagc catagtgaag acagtgatg  gacagccgac    2880
ggcagttggg attcgtgaat tgctgccctc tggttatgtg tgggagggct aagcacaatt    2940
cgagctcggt acctttaaga ccaatgactt acaaggcagc tgtagatctt agccactttt    3000
taaaagaaaa gggggactg  gaagggctaa ttcactccca acgaagacaa gatctgcttt    3060
ttgcttgtac tgggtctctc tggttagacc agatctgagc ctgggagctc tctggctaac    3120
tagggaaccc actgcttaag cctcaataaa gcttgccttg agtgcttcaa gtagtgtgtg    3180
cccgtctgtt gtgtgactct ggtaactaga gatccctcag accctttag  tcagtgtgga    3240
aaatctctag cagtagtagt tcatgtcatc ttattattca gtatttataa cttgcaaaga    3300
aatgaatatc agagagtgag aggaacttgt ttattgcagc ttataatggt tacaaataaa    3360
gcaatagcat cacaaatttc acaaataaag cattttttc  actgcattct agttgtggtt    3420
tgtccaaact catcaatgta tcttatcatg tctggctcta gctatcccgc ccctaactcc    3480
gcccatcccg ccctaactc  cgcccagttc cgcccattct ccgccccatg gctgactaat    3540
ttttttatt  tatgcagagg ccgaggccgc ctcggcctct gagctattcc agaagtagtg    3600
aggaggcttt tttggaggcc tagggacgta cccaattcgc cctatagtga gtcgtattac    3660
gcgcgctcac tggccgtcgt tttacaacgt cgtgactggg aaaaccctgg cgttacccaa    3720
cttaatcgcc ttgcagcaca tcccccttc  gccagctggc gtaatagcga agaggcccgc    3780
accgatcgcc cttcccaaca gttgcgcagc ctgaatggcg aatgggacgc gccctgtagc    3840
ggcgcattaa gcgcggcggg tgtggtggtt acgcgcagcg tgaccgctac acttgccagc    3900
gccctagcgc ccgctccttt cgctttcttc ccttcctttc tcgccacgtt cgccggcttt    3960
ccccgtcaag ctctaaatcg ggggctccct ttagggttcc gatttagtgc tttacggcac    4020
ctcgacccca aaaaacttga ttagggtgat ggttcacgta gtgggccatc gccctgatag    4080
acggttttc  gccctttgac gttggagtcc acgttcttta atagtggact cttgttccaa    4140
actggaacaa cactcaaccc tatctcggtc tattcttttg atttataagg gattttgccg    4200
atttcggcct attggttaaa aaatgagctg atttaacaaa aatttaacgc gaattttaac    4260
aaaatattaa cgcttacaat ttaggtggca cttttcgggg aaatgtgcgc ggaaccccta    4320
tttgtttatt tttctaaata cattcaaata tgtatccgct catgagacaa taaccctgat    4380
aaatgcttca ataatattga aaaggaaga  gtatgagtat tcaacatttc cgtgtcgccc    4440
ttattccctt ttttgcggca ttttgccttc ctgtttttgc tcacccagaa acgctggtga    4500
aagtaaaaga tgctgaagat cagttgggtg cacgagtggg ttacatcgaa ctggatctca    4560
acagcggtaa gatccttgag agttttcgcc ccgaagaacg ttttccaatg atgagcactt    4620
ttaaagttct gctatgtggc gcggtattat cccgtattga cgccgggcaa gagcaactcg    4680
gtcgccgcat acactattct cagaatgact tggttgagta ctcaccagtc acagaaaagc    4740
atcttacgga tggcatgaca gtaagagaat tatgcagtgc tgccataacc atgagtgata    4800
acactgcggc caacttactt ctgacaacga tcggaggacc gaaggagcta accgcttttt    4860
tgcacaacat gggggatcat gtaactcgcc ttgatcgttg gaaccggag  ctgaatgaag    4920
ccataccaaa cgacgagcgt gacaccacga tgcctgtagc aatggcaaca acgttgcgca    4980
aactattaac tggcgaacta cttactctag cttcccggca acaattaata gactggatgg    5040
```

| aggcggataa | agttgcagga | ccacttctgc | gctcggccct | tccggctggc | tggtttattg | 5100 |
| ctgataaatc | tggagccggt | gagcgtgggt | ctcgcggtat | cattgcagca | ctggggccag | 5160 |
| atggtaagcc | ctcccgtatc | gtagttatct | acacgacggg | gagtcaggca | actatggatg | 5220 |
| aacgaaatag | acagatcgct | gagataggtg | cctcactgat | taagcattgg | taactgtcag | 5280 |
| accaagttta | ctcatatata | ctttagattg | atttaaaact | tcattttaa | tttaaaagga | 5340 |
| tctaggtgaa | gatccttttt | gataatctca | tgaccaaaat | cccttaacgt | gagttttcgt | 5400 |
| tccactgagc | gtcagacccc | gtagaaaaga | tcaaaggatc | ttcttgagat | cctttttttc | 5460 |
| tgcgcgtaat | ctgctgcttg | caaacaaaaa | aaccaccgct | accagcggtg | gtttgtttgc | 5520 |
| cggatcaaga | gctaccaact | cttttccga | aggtaactgg | cttcagcaga | gcgcagatac | 5580 |
| caaatactgt | tcttctagtg | tagccgtagt | taggccacca | cttcaagaac | tctgtagcac | 5640 |
| cgcctacata | cctcgctctg | ctaatcctgt | taccagtggc | tgctgccagt | ggcgataagt | 5700 |
| cgtgtcttac | cgggttggac | tcaagacgat | agttaccgga | taaggcgcag | cggtcgggct | 5760 |
| gaacggggg | ttcgtgcaca | cagcccagct | tggagcgaac | gacctacacc | gaactgagat | 5820 |
| acctacagcg | tgagctatga | gaaagcgcca | cgcttcccga | agggagaaag | gcggacaggt | 5880 |
| atccggtaag | cggcagggtc | ggaacaggag | agcgcacgag | ggagcttcca | gggggaaacg | 5940 |
| cctggtatct | ttatagtcct | gtcgggtttc | gccacctctg | acttgagcgt | cgatttttgt | 6000 |
| gatgctcgtc | agggggcgg | agcctatgga | aaaacgccag | caacgcggcc | ttttacggt | 6060 |
| tcctggcctt | ttgctggcct | tttgctcaca | tgttctttcc | tgcgttatcc | cctgattctg | 6120 |
| tggataaccg | tattaccgcc | tttgagtgag | ctgataccgc | tcgccgcagc | cgaacgaccg | 6180 |
| agcgcagcga | gtcagtgagc | gaggaagcgg | aagagcgccc | aatacgcaaa | ccgcctctcc | 6240 |
| ccgcgcgttg | gccgattcat | taatgcagct | ggcacgacag | gtttcccgac | tggaaagcgg | 6300 |
| gcagtgagcg | caacgcaatt | aatgtgagtt | agctcactca | ttaggcaccc | caggctttac | 6360 |
| actttatgct | tccggctcgt | atgttgtgtg | gaattgtgag | cggataacaa | tttcacacag | 6420 |
| gaaacagcta | tgaccatgat | tacgccaagc | gcgcaattaa | ccctcactaa | agggaacaaa | 6480 |
| agctggagct | gcaagctt | | | | | 6498 |

<210> SEQ ID NO 9
<211> LENGTH: 6702
<212> TYPE: DNA
<213> ORGANISM: Artificial
<220> FEATURE:
<223> OTHER INFORMATION: Modified Lentivirus (pLenti-U6-hrGFP)

<400> SEQUENCE: 9

| aatgtagtct | tatgcaatac | tcttgtagtc | ttgcaacatg | gtaacgatga | gttagcaaca | 60 |
| tgccttacaa | ggagagaaaa | agcaccgtgc | atgccgattg | gtggaagtaa | ggtggtacga | 120 |
| tcgtgcctta | ttaggaaggc | aacagacggg | tctgacatgg | attggacgaa | ccactgaatt | 180 |
| gccgcattgc | agagatattg | tatttaagtg | cctagctcga | tacataaacg | ggtctctctg | 240 |
| gttagaccag | atctgagcct | gggagctctc | tggctaacta | gggaacccac | tgcttaagcc | 300 |
| tcaataaagc | ttgccttgag | tgcttcaagt | agtgtgtgcc | cgtctgttgt | gtgactctgg | 360 |
| taactagaga | tccctcagac | cctttagtc | agtgtggaaa | atctctagca | gtggcgcccg | 420 |
| aacagggact | tgaaagcgaa | agggaaacca | gaggagctct | ctcgacgcag | gactcggctt | 480 |
| gctgaagcgc | gcacggcaag | aggcgagggg | cggcgactgg | tgagtacgcc | aaaaattttg | 540 |

-continued

```
actagcggag gctagaagga gagagatggg tgcgagagcg tcagtattaa gcgggggaga     600
attagatcgc gatgggaaaa aattcggtta aggccagggg gaaagaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagataccc taaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620
agttttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtaatcgat    1800
tttcccatga ttccttcata tttgcatata cgatacaagg ctgttagaga gataattaga    1860
attaatttga ctgtaaacac aaagatatta gtacaaaata cgtgacgtag aaagtaataa    1920
tttcttgggt agtttgcagt ttttaaaatt atgttttaaa atggactatc atatgcttac    1980
cgtaacttga aagtatttcg atttcttggc tttatatatc ttgtggaaag gacgaaacac    2040
cgaattcacc ggtcggttag taatgagttt ggaattaatt ctgtggaatg tgtgtcagtt    2100
agggtgtgga aagtccccag gctccccagg caggcagaag tatgcaaagc atgcatctca    2160
attagtcagc aaccaggtgt ggaaagtccc caggctcccc agcaggcaga agtatgcaaa    2220
gcatgcatct caattagtca gcaaccatag tcccgcccct aactccgccc atcccgcccc    2280
taactccgcc cagttccgcc cattctccgc cccatggctg actaatttt tttatttatg    2340
cagaggccga ggccgcctct gcctctgagc tattccagaa gtagtgagga ggctttttg    2400
gaggcctagg cttttgcaaa aagctcccgg gatggtgagc aagcagatcc tgaagaacac    2460
cggcctgcag gagatcatga gcttcaaggt gaacctggag ggcgtggtga acaaccacgt    2520
gttcaccatg gagggctgcg gcaagggcaa catcctgttc ggcaaccagc tggtgcagat    2580
ccgcgtgacc aagggcgccc ccctgccctt cgccttcgac atcctgagcc ccgccttcca    2640
gtacggcaac cgcaccttca ccaagtaccc cgaggacatc agcgacttct tcatccagag    2700
cttccccgcc ggcttcgtgt acgagcgcac cctgcgctac gaggacggcg gcctggtgga    2760
gatccgcagc gacatcaacc tgatcgagga gatgttcgtg taccgcgtgg agtacaaggg    2820
ccgcaacttc cccaacgacg gccccgtgat gaagaagacc atcaccggcc tgcagccag    2880
cttcgaggtg gtgtacatga acgacggcgt gctggtgggc caggtgatcc tggtgtaccg    2940
```

```
cctgaacagc ggcaagttct acagctgcca catgcgcacc ctgatgaaga gcaagggcgt    3000
ggtgaaggac ttccccgagt accacttcat ccagcaccgc ctggagaaga cctacgtgga    3060
ggacggcggc ttcgtggagc agcacgagac cgccatcgcc cagctgacca gcctgggcaa    3120
gccccctggc agcctgcacg agtgggtgta aggtaccttt aagaccaatg acttacaagg    3180
cagctgtaga tcttagccac ttttaaaag aaaaggggg actggaaggg ctaattcact    3240
cccaacgaag acaagatctg cttttgctt gtactgggtc tctctggtta gaccagatct    3300
gagcctggga gctctctggc taactaggga acccactgct taagcctcaa taaagcttgc    3360
cttgagtgct tcaagtagtg tgtgcccgtc tgttgtgtga ctctggtaac tagagatccc    3420
tcagaccctt ttagtcagtg tggaaaatct ctagcagtag tagttcatgt catcttatta    3480
ttcagtattt ataacttgca aagaaatgaa tatcagagag tgagaggaac ttgtttattg    3540
cagcttataa tggttacaaa taaagcaata gcatcacaaa tttcacaaat aaagcatttt    3600
tttcactgca ttctagttgt ggtttgtcca aactcatcaa tgtatcttat catgtctggc    3660
tctagctatc ccgcccctaa ctccgcccat ccgcccccta actccgccca gttccgccca    3720
ttctccgccc catggctgac taattttttt tatttatgca gaggccgagg ccgcctcggc    3780
ctctgagcta ttccagaagt agtgaggagg ctttttgga ggcctaggga cgtacccaat    3840
tcgccctata gtgagtcgta ttacgcgcgc tcactggccg tcgttttaca acgtcgtgac    3900
tgggaaaacc ctggcgttac ccaacttaat cgccttgcag cacatccccc tttcgccagc    3960
tggcgtaata gcgaagaggc ccgcaccgat cgcccttccc aacagttgcg cagcctgaat    4020
ggcgaatggg acgcgccctg tagcggcgca ttaagcgcgg cgggtgtggt ggttacgcgc    4080
agcgtgaccg ctacacttgc cagcgcccta gcgcccgctc ctttcgcttt cttcccttcc    4140
tttctcgcca cgttcgccgg ctttccccgt caagctctaa atcggggct ccctttaggg    4200 ttccgattta gtgctttacg gcacctcgac cccaaaaaac ttgattaggg tgatggttca    4260
cgtagtgggc catcgccctg atagacggtt tttcgccctt gacgttgga gtccacgttc    4320 tttaatagtg gactcttgtt ccaaactgga acaacactca accctatctc ggtctattct    4380
tttgatttat aagggatttt gccgatttcg gcctattggt taaaaaatga gctgatttaa    4440
caaaaattta acgcgaattt taacaaaata ttaacgctta caatttaggt ggcacttttc    4500
ggggaaatgt gcgcggaacc cctatttgtt tatttttcta aatacattca aatatgtatc    4560
cgctcatgag acaataaccc tgataaatgc ttcaataata ttgaaaaagg aagagtatga    4620
gtattcaaca tttccgtgtc gcccttattc cctttttgc ggcattttgc cttcctgttt    4680
ttgctcaccc agaaacgctg gtgaaagtaa aagatgctga agatcagttg ggtgcacgag    4740
tgggttacat cgaactggat ctcaacagcg gtaagatcct tgagagtttt cgccccgaag    4800
aacgttttcc aatgatgagc acttttaaag ttctgctatg tggcgcggta ttatcccgta    4860
ttgacgccgg gcaagagcaa ctcggtcgcc gcatacacta ttctcagaat gacttggttg    4920
agtactcacc agtcacagaa aagcatctta cggatggcat gacagtaaga gaattatgca    4980
gtgctgccat aaccatgagt gataacactg cggccaactt acttctgaca acgatcggag    5040
gaccgaagga gctaaccgct tttttgcaca acatggggga tcatgtaact cgccttgatc    5100
gttgggaacc ggagctgaat gaagccatac caaaacgacga gcgtgacacc acgatgcctg    5160
tagcaatggc aacaacgttg cgcaaactat taactggcga actacttact ctagcttccc    5220
ggcaacaatt aatagactgg atggaggcgg ataaagttgc aggaccactt ctgcgctcgg    5280
```

-continued

```
ccottccggc tggctggttt attgctgata aatctggagc cggtgagcgt gggtctcgcg    5340
gtatcattgc agcactgggg ccagatggta agccctcccg tatcgtagtt atctacacga    5400
cggggagtca ggcaactatg gatgaacgaa atagacagat cgctgagata ggtgcctcac    5460
tgattaagca ttggtaactg tcagaccaag tttactcata tactttag attgatttaa     5520 aacttcattt ttaatttaaa aggatctagg tgaagatcct ttttgataat ctcatgacca   5580 aaatcccta acgtgagttt cgttccact gagcgtcaga ccccgtagaa aagatcaaag     5640
gatcttcttg agatcctttt tttctgcgcg taatctgctg cttgcaaaca aaaaaaccac   5700
cgctaccagc ggtggtttgt tgccggatc aagagctacc aactctttt ccgaaggtaa    5760 ctggcttcag cagagcgcag ataccaaata ctgttcttct agtgtagccg tagttaggcc   5820
accacttcaa gaactctgta gcaccgccta catacctcgc tctgctaatc ctgttaccag   5880
tggctgctgc cagtggcgat aagtcgtgtc ttaccgggtt ggactcaaga cgatagttac   5940
cggataaggc gcagcggtcg ggctgaacg ggggttcgtg cacacagccc agcttggagc    6000
gaacgaccta caccgaactg agatacctac agcgtgagct atgagaaagc gccacgcttc   6060
ccgaagggag aaaggcggac aggtatccgg taagcggcag ggtcggaaca ggagagcgca   6120
cgagggagct ccaggggga acgcctggt atctttatag tcctgtcggg tttcgccacc    6180
tctgacttga gcgtcgattt ttgtgatgct cgtcagggg gcggagccta tggaaaaacg   6240
ccagcaacgc ggcctttta cggttcctgg cctttgctg gcttttgct cacatgttct     6300 ttcctgcgtt atccctgat tctgtggata accgtattac cgcctttgag tgagctgata   6360
ccgctcgccg cagccgaacg accgagcgca gcgagtcagt gagcgaggaa gcggaagagc   6420
gcccaatacg caaaccgcct ctccccgcgc gttggccgat tcattaatgc agctggcacg   6480
acaggtttcc cgactggaaa gcgggcagtg agcgcaacgc aattaatgtg agttagctca   6540
ctcattaggc accccaggct ttacacttta tgcttccggc tcgtatgttg tgtggaattg   6600
tgagcggata acaatttcac acaggaaaca gctatgacca tgattacgcc aagcgcgcaa   6660
ttaaccctca ctaaagggaa caaaagctgg agctgcaagc tt                     6702
```

<210> SEQ ID NO 10
<211> LENGTH: 7244
<212> TYPE: DNA
<213> ORGANISM: Artificial
<220> FEATURE:
<223> OTHER INFORMATION: MSCV vector (MSCV-U6-Hygro)

<400> SEQUENCE: 10

```
tgaaagaccc cacctgtagg tttggcaagc tagcttaagt aacgccattt tgcaaggcat      60
ggaaaataca taactgagaa tagagaagtt cagatcaagg ttaggaacag agagacagca    120
gaatatgggc caaacaggat atctgtggta agcagttcct gccccggctc agggccaaga   180
acagatggtc cccagatgcg gtcccgccct cagcagtttc tagagaacca tcagatgttt    240
ccagggtgcc ccaaggacct gaaatgaccc tgtgccttat ttgaactaac caatcagttc   300
gcttctcgct tctgttcgcg cgcttctgct ccccgagctc aataaaagag cccacaaccc   360
ctcactcggc gcgccagtcc tccgatagac tgcgtcgccc gggtacccgt attcccaata   420
aagcctcttg ctgtttgcat ccgaatcgtg gactcgctga tccttgggag ggtctcctca   480
gattgattga ctgcccacct cgggggtctt tcatttggag gttccaccga gatttggaga   540
cccctgccca gggaccaccg accccccgc cgggaggtaa gctggccagc ggtcgtttcg   600
tgtctgtctc tgtctttgtg cgtgtttgtg ccggcatcta atgtttgcgc ctgcgtctgt    660
```

```
actagttagc taactagctc tgtatctggc ggacccgtgg tggaactgac gagttctgaa    720
cacccggccg caaccctggg agacgtccca gggactttgg gggccgtttt tgtggcccga    780
cctgaggaag ggagtcgatg tggaatccga ccccgtcagg atatgtggtt ctggtaggag    840
acgagaacct aaaacagttc ccgcctccgt ctgaattttt gctttcggtt tggaaccgaa    900
gccgcgcgtc ttgtctgctg cagcgctgca gcatcgttct gtgttgtctc tgtctgactg    960
tgtttctgta tttgtctgaa aattagggcc agactgttac cactcccttta agtttgaccct   1020
taggtcactg gaaagatgtc gagcggatcg ctcacaacca gtcggtagat gtcaagaaga   1080
gacgttgggt taccttctgc tctgcagaat ggccaacctt taacgtcgga tggccgcgag   1140
acggcacctt taaccgagac ctcatcaccc aggttaagat caaggtcttt tcacctggcc   1200
cgcatggaca cccagaccag gtcccctaca tcgtgacctg ggaagccttg gcttttgacc   1260
cccctccctg ggtcaagccc tttgtacacc ctaagcctcc gcctcctctt cctccatccg   1320
ccccgtctct cccccttgaa cctcctcgtt cgaccccgcc tcgtatcctc cctttatcca   1380
gccctcactc cttctctagg cgccggaatt agatctttcc catgattcct tcatatttgc   1440
atatacgata caaggctgtt agagagataa ttagaattaa tttgactgta aacacaaaga   1500
tattagtaca aaatacgtga cgtagaaagt aataatttct tgggtagttt gcagttttta   1560
aaattatgtt ttaaaatgga ctatcatatg cttaccgtaa cttgaaagta tttcgatttc   1620
ttggctttat atatcttgtg gaaaggacga acacctctg aggttaacgg atccgcggcc   1680
gcacgcgtgt taacgaattc taccgggtag gggaggcgct tttcccaagg cagtctggag   1740
catgcgcttt agcagccccg ctgggcactt ggcgctacac aagtggcctc tggcctcgca   1800
cacattccac atccaccggt aggcgccaac cggctccgtt ctttggtggc ccttcgcgc   1860
caccttctac tcctccccta gtcaggaagt tcccccccgc cccgcagctc gcgtcgtgca   1920
ggacgtgaca aatggaagta gcacgtctca ctagtctcgt gcagatggac agcaccgctg   1980
agcaatggaa gcgggtaggc ctttgggca gcggccaata gcagctttgc tccttcgctt   2040
tctgggctca gaggctggga aggggtgggt ccggggggcgg gctcagggc gggctcaggg   2100
gcggggcggg cgcccgaagg tcctccggag gcccggcatt ctgcacgctt caaaagcgca   2160
cgtctgccgc gctgttctcc tcttcctcat ctccgggcct ttcgacctgc atcccgccac   2220
catgaaaaag cctgaactca ccgcgacgtc tgtcgagaag tttctgatcg aaaagttcga   2280
cagcgtctcc gacctgatgc agctctcgga gggcgaagaa tctcgtgctt tcagcttcga   2340
tgtaggaggg cgtggatatg tcctgcgggt aaatagctgc gccgatggtt tctacaaaga   2400
tcgttatgtt tatcggcact ttgcatcggc cgcgctcccg attccggaag tgcttgacat   2460
tggggaattc agcgagagcc tgacctattg catctcccgc cgtgcacagg gtgtcacgtt   2520
gcaagacctg cctgaaaccg aactgcccgc tgttctgcag ccggtcgcgg aggccatgga   2580
tgcgatcgct gcggccgatc ttagccagac gagcgggttc ggcccattcg accgcaagg   2640
aatcggtcaa tacactacat ggcgtgattt catatgcgcg attgctgatc ccatgtgta   2700
tcactggcaa actgtgatgg acgacaccgt cagtgcgtcc gtcgcgcagg ctctcgatga   2760
gctgatgctt tgggccgagg actgccccga agtccggcac ctcgtgcacg cggatttcgg   2820
ctccaacaat gtcctgacgg acaatggccg cataacagcg gtcattgact ggagcgaggc   2880
gatgttcggg gattcccaat acgaggtcgc caacatcttc ttctggaggc cgtggttggc   2940
ttgtatggag cagcagacgc gctacttcga gcggaggcat ccggagcttg caggatcgcc   3000
```

```
gcggctccgg ggcgtatatg ctccgcattg gtcttgacca actctatcag agcttggttg    3060
acggcaattt cgatgatgca gcttgggcgc agggtcgatg cgacgcaatc gtccgatccg    3120
gagccgggac tgtcgggcgt acacaaatcg cccgcagaag cgcggccgtc tggaccgatg    3180
gctgtgtaga agtactcgcc gatagtggaa accgacgccc cagcactcgt ccgagggcaa    3240
aggaatagag tagatgccga ccgaacaaga gctgatttcg agaacgcctc agccagcaac    3300
tcgcgcgagc ctagcaaggc aaatgcgaga gaacggcctt acgcttggtg gcacagttct    3360
cgtccacagt tcgctaagct cgctcggctg ggtcgcggga gggccggtcg cagtgattca    3420
ggcccttctg gattgtgttg gtccccaggg cacgattgtc atgcccacgc actcgggtga    3480
tctgactgat cccgcagatt ggagatcgcc gcccgtgcct gccgattggg tgcagatccg    3540
tcgacctgca gccaagctta tcgataaaat aaaagatttt atttagtctc cagaaaaagg    3600
ggggaatgaa agaccccacc tgtaggtttg gcaagctagc ttaagtaacg ccattttgca    3660
aggcatggaa aatacataac tgagaataga gaagttcaga tcaaggttag gaacagagag    3720
acagcagaat atgggccaaa caggatatct gtggtaagca gttcctgccc cggctcaggg    3780
ccaagaacag atggtcccca gatgcggtcc cgccctcagc agtttctaga gaaccatcag    3840
atgtttccag ggtgccccaa ggacctgaaa tgaccctgtg ccttatttga actaaccaat    3900
cagttcgctt ctcgcttctg ttcgcgcgct tctgctcccc gagctcaata aaagagccca    3960
caacccctca ctcggcgcgc cagtcctccg atagactgcg tcgcccgggt accgtgtat    4020 ccaataaacc ctcttgcagt tgcatccgac ttgtggtctc gctgttcctt gggagggtct    4080
cctctgagtg attgactacc cgtcagcggg ggtctttcat gggtaacagt ttcttgaagt    4140
tggagaacaa cattctgagg gtaggagtcg aatattaagt aatcctgact caattagcca    4200
ctgttttgaa tccacatact ccaatactcc tgaaatagtt cattatggac agcgcagaag    4260
agctggggag aattaattcg taatcatggt catagctgtt tcctgtgtga aattgttatc    4320
cgctcacaat tccacacaac atacgagccg gaagcataaa gtgtaaagcc tggggtgcct    4380
aatgagtgag ctaactcaca ttaattgcgt tgcgctcact gcccgctttc cagtcgggaa    4440
acctgtcgtg ccagctgcat taatgaatcg gccaacgcgc ggggagaggc ggtttgcgta    4500
ttgggcgctc ttccgcttcc tcgctcactg actcgctgcg ctcggtcgtt cggctgcggc    4560
gagcggtatc agctcactca aaggcggtaa tacggttatc cacagaatca ggggataacg    4620
caggaaagaa catgtgagca aaaggccagc aaaaggccag gaaccgtaaa aaggccgcgt    4680
tgctggcgtt tttccatagg ctccgccccc ctgacgagca tcacaaaaat cgacgctcaa    4740
gtcagaggtg gcgaaacccg acaggactat aaagatacca ggcgtttccc cctggaagct    4800
ccctcgtgcg ctctcctgtt ccgaccctgc cgcttaccgg atacctgtcc gcctttctcc    4860
cttcgggaag cgtggcgctt tctcatagct cacgctgtag gtatctcagt tcggtgtagg    4920
tcgttcgctc caagctgggc tgtgtgcacg aaccccccgt tcagcccgac cgctgcgcct    4980
tatccggtaa ctatcgtctt gagtccaacc cggtaagaca cgacttatcg ccactggcag    5040
cagccactgg taacaggatt agcagagcga ggtatgtagg cggtgctaca gagttcttga    5100
agtggtggcc taactacggc tacactagaa ggacagtatt tggtatctgc gctctgctga    5160
agccagttac cttcggaaaa agagttggta gctcttgatc cggcaaacaa accaccgctg    5220
gtagcggtgg tttttttgtt tgcaagcagc agattacgcg cagaaaaaaa ggatctcaag    5280
aagatccttt gatcttttct acggggtctg acgctcagtg gaacgaaaac tcacgttaag    5340
ggattttggt catgagatta tcaaaaagga tcttcaccta gatcctttta aattaaaaat    5400
```

-continued

```
gaagttttaa atcaatctaa agtatatatg agtaaacttg gtctgacagt taccaatgct      5460
taatcagtga ggcacctatc tcagcgatct gtctatttcg ttcatccata gttgcctgac      5520
tccccgtcgt gtagataact acgatacggg agggcttacc atctggcccc agtgctgcaa      5580
tgataccgcg agacccacgc tcaccggctc cagatttatc agcaataaac cagccagccg      5640
gaagggccga gcgcagaagt ggtcctgcaa ctttatccgc ctccatccag tctattaatt      5700
gttgccggga agctagagta agtagttcgc cagttaatag tttgcgcaac gttgttgcca      5760
ttgctacagg catcgtggtg tcacgctcgt cgtttggtat ggcttcattc agctccggtt      5820
cccaacgatc aaggcgagtt acatgatccc ccatgttgtg caaaaaagcg gttagctcct      5880
tcggtcctcc gatcgttgtc agaagtaagt tggccgcagt gttatcactc atggttatgg      5940
cagcactgca taattctctt actgtcatgc catccgtaag atgcttttct gtgactggtg      6000
agtactcaac caagtcattc tgagaatagt gtatgcggcg accgagttgc tcttgcccgg      6060
cgtcaatacg ggataatacc gcgccacata gcagaacttt aaaagtgctc atcattggaa      6120
aacgttcttc ggggcgaaaa ctctcaagga tcttaccgct gttgagatcc agttcgatgt      6180
aacccactcg tgcacccaac tgatcttcag catcttttac tttcaccagc gtttctgggt      6240
gagcaaaaac aggaaggcaa aatgccgcaa aaaagggaat aagggcgaca cggaaatgtt      6300
gaatactcat actcttcctt tttcaatatt attgaagcat ttatcagggt tattgtctca      6360
tgagcggata catatttgaa tgtatttaga aaaataaaca aatagggggtt ccgcgcacat      6420 ttccccgaaa agtgccacct gacgtctaag aaaccattat tatcatgaca ttaacctata      6480
aaaataggcg tatcacgagg ccctttcgtc tcgcgcgttt cggtgatgac ggtgaaaacc      6540
tctgacacat gcagctcccg gagacggtca cagcttgtct gtaagcggat gccgggagca      6600
gacaagcccg tcagggcgcg tcagcgggtg ttggcgggtg tcgggctgg cttaactatg      6660 cggcatcaga gcagattgta ctgagagtgc accatatgcg gtgtgaaata ccgcacagat      6720
gcgtaaggag aaaataccgc atcaggcgcc attcgccatt caggctgcgc aactgttggg      6780
aagggcgatc ggtgcgggcc tcttcgctat tacgccagct ggcgaaaggg ggatgtgctg      6840
caaggcgatt aagttgggta acgccagggt tttcccagtc acgacgttgt aaaacgacgg      6900
cgcaaggaat ggtgcatgca aggagatggc gcccaacagt cccccggcca cggggcctgc      6960
caccataccc acgccgaaac aagcgctcat gagcccgaag tggcgagccc gatcttcccc      7020
atcggtgatg tcggcgatat aggcgccagc aaccgcacct gtggcgccgg tgatgccggc      7080
cacgatgcgt ccggcgtaga ggcgattagt ccaatttgtt aaagacagga tatcagtggt      7140
ccaggctcta gttttgactc aacaatatca ccagctgaag cctatagagt acgagccata      7200
gataaaataa aagatttat ttagtctcca gaaaaagggg ggaa      7244
```

<210> SEQ ID NO 11
<211> LENGTH: 6561
<212> TYPE: DNA
<213> ORGANISM: Artificial
<220> FEATURE:
<223> OTHER INFORMATION: MSCV Vector (MSCV-U6-Puro)

<400> SEQUENCE: 11

```
tgaaagaccc cacctgtagg tttggcaagc tagcttaagt aacgccattt tgcaaggcat      60
ggaaaataca taactgagaa tagagaagtt cagatcaagg ttaggaacag agagacagca      120
gaatatgggc caaacaggat atctgtggta agcagttcct gccccggctc agggccaaga      180
```

-continued

```
acagatggtc cccagatgcg gtcccgccct cagcagtttc tagagaacca tcagatgttt      240
ccagggtgcc ccaaggacct gaaatgaccc tgtgccttat ttgaactaac caatcagttc      300
gcttctcgct tctgttcgcg cgcttctgct ccccgagctc aataaaagag cccacaaccc      360
ctcactcggc gcgccagtcc tccgatagac tgcgtcgccc gggtacccgt attcccaata      420
aagcctcttg ctgtttgcat ccgaatcgtg gactcgctga tccttgggag ggtctcctca      480
gattgattga ctgcccacct cgggggtctt tcatttggag gttccaccga gatttggaga      540
cccctgccca gggaccaccg acccccccgc cgggaggtaa gctggccagc ggtcgtttcg      600
tgtctgtctc tgtctttgtg cgtgtttgtg ccggcatcta atgtttgcgc ctgcgtctgt      660
actagttagc taactagctc tgtatctggc ggacccgtgg tggaactgac gagttctgaa      720
cacccggccg caaccctggg agacgtccca gggactttgg gggccgtttt tgtggcccga      780
cctgaggaag ggagtcgatg tggaatccga ccccgtcagg atatgtggtt ctggtaggag      840
acgagaacct aaaacagttc ccgcctccgt ctgaattttt gctttcggtt tggaaccgaa      900
gccgcgcgtc ttgtctgctg cagcgctgca gcatcgttct gtgttgtctc tgtctgactg      960
tgtttctgta tttgtctgaa aattagggcc agactgttac cactcccctta agtttgacct    1020 taggtcactg gaaagatgtc gagcggatcg ctcacaacca gtcggtagat gtcaagaaga     1080
gacgttgggt taccttctgc tctgcagaat ggccaacctt taacgtcgga tggccgcgag     1140
acggcacctt taaccgagac ctcatcaccc aggttaagat caaggtcttt tcacctggcc     1200
cgcatggaca cccagaccag gtcccctaca tcgtgacctg ggaagccttg gcttttgacc     1260
cccctccctg ggtcaagccc tttgtacacc ctaagcctcc gcctcctctt cctccatccg     1320 cccgtctct cccccttgaa cctcctcgtt cgacccccgcc tcgatcctcc ctttatccag     1380
ccctcactcc ttctctaggc gccggaatta gatctttccc atgattcctt catatttgca     1440
tatacgatac aaggctgtta gagagataat tagaattaat ttgactgtaa acacaaagat     1500
attagtacaa aatacgtgac gtagaaagta ataatttctt gggtagtttg cagtttttaa     1560
aattatgttt taaaatggac tatcatatgc ttaccgtaac ttgaaagtat ttcgatttct     1620
tggctttata tatcttgtgg aaaggacgaa acacctctga ggttaacgga tccgcggccg     1680
cacgcgtgtt aacgaattct accgggtagg ggaggcgctt ttcccaaggc agtctggagc     1740
atgcgcttta gcagccccgc tgggcacttg gcgctacaca agtggcctct ggcctcgcac     1800
acattccaca tccaccggta ggcgccaacc ggctccgttc tttggtggcc ccttcgcgcc     1860
accttctact cctcccctag tcaggaagtt cccccccgcc ccgcagctcg cgtcgtgcag     1920
gacgtgacaa atggaagtag cacgtctcac tagtctcgtg cagatggaca gcaccgctga     1980
gcaatggaag cgggtaggcc tttggggcag cggccaatag cagctttgct ccttcgcttt     2040
ctgggctcag aggctgggaa ggggtgggtc cggggcggg ctcaggggcg ggctcagggg      2100
cggggcgggc gcccgaaggt cctccggagg cccggcattc tgcacgcttc aaaagcgcac     2160
gtctgccgcg ctgttctcct cttcctcatc tccgggcctt tcgacctgca gcccaagctt     2220
accatgaccg agtacaagcc cacggtgcgc ctcgccaccc gcgacgacgt ccccagggcc     2280
gtacgcaccc tcgccgccgc gttcgccgac taccccgcca cgcgccacac cgtcgatccg     2340
gaccgccaca tcgagcgggt caccgagctg caagaactct tcctcacgcg cgtcgggctc     2400
gacatcggca aggtgtgggt cgcggacgac ggcgccgcgg tggcggtctg gaccacgccg     2460
gagagcgtcg aagcggggc ggtgttcgcc gagatcggcc cgcgcatggc cgagttgagc     2520
ggttcccggc tggccgcgca gcaacagatg gaaggcctcc tggcgccgca ccggcccaag     2580
```

```
gagcccgcgt ggttcctggc caccgtcggc gtctcgcccg accaccaggg caagggtctg   2640
ggcagcgccg tcgtgctccc cggagtggag gcggccgagc gcgccggggt gcccgccttc   2700
ctggagacct ccgcgccccg caacctcccc ttctacgagc ggctcggctt caccgtcacc   2760
gccgacgtcg aggtgcccga aggaccgcgc acctggtgca tgacccgcaa gcccggtgcc   2820
tgacgcccgc cccacgaccc gcagcgcccg accgaaagga gcgcacgacc ccatgcatcg   2880
ataaaataaa agattttatt tagtctccag aaaaaggggg aatgaaaga ccccacctgt    2940 aggtttggca agctagctta agtaacgcca ttttgcaagg catggaaaat acataactga   3000
gaatagagaa gttcagatca aggttaggaa cagagagaca gcagaatatg ggccaaacag   3060
gatatctgtg gtaagcagtt cctgccccgg ctcagggcca agaacagatg gtccccagat   3120
gcggtcccgc cctcagcagt ttctagagaa ccatcagatg tttccagggt gccccaagga   3180
cctgaaatga ccctgtgcct tatttgaact aaccaatcag ttcgcttctc gcttctgttc   3240
gcgcgcttct gctccccgag ctcaataaaa gagcccacaa cccctcactc ggcgcgccag   3300
tcctccgata gactgcgtcg cccgggtacc cgtgtatcca ataaaccctc ttgcagttgc   3360
atccgacttg tggtctcgct gttccttggg agggtctcct ctgagtgatt gactacccgt   3420
cagcgggggt ctttcatggg taacagtttc ttgaagttgg agaacaacat tctgagggta   3480
ggagtcgaat attaagtaat cctgactcaa ttagccactg ttttgaatcc acatactcca   3540
atactcctga aatagttcat tatgacagc gcagaagagc tggggagaat taattcgtaa   3600
tcatggtcat agctgtttcc tgtgtgaaat tgttatccgc tcacaattcc acacaacata   3660
cgagccggaa gcataaagtg taaagcctgg ggtgcctaat gagtgagcta actcacatta   3720
attgcgttgc gctcactgcc cgcttttcag tcgggaaacc tgtcgtgcca gctgcattaa   3780
tgaatcggcc aacgcgcggg gagaggcggt ttgcgtattg ggcgctcttc cgcttcctcg   3840
ctcactgact cgctgcgctc ggtcgttcgg ctgcggcgag cggtatcagc tcactcaaag   3900
gcggtaatac ggttatccac agaatcaggg gataacgcag gaaagaacat gtgagcaaaa   3960
ggccagcaaa aggccaggaa ccgtaaaaag gccgcgttgc tggcgttttt ccataggctc   4020
cgcccccctg acgagcatca caaaaatcga cgctcaagtc agaggtggcg aaacccgaca   4080
ggactataaa gataccaggc gtttccccct ggaagctccc tcgtgcgctc tcctgttccg   4140
accctgccgc ttaccggata cctgtccgcc tttctccctt cgggaagcgt ggcgctttct   4200
catagctcac gctgtaggta tctcagttcg gtgtaggtcg ttcgctccaa gctgggctgt   4260
gtgcacgaac cccccgttca gcccgaccgc tgcgccttat ccggtaacta tcgtcttgag   4320
tccaacccgg taagacacga cttatcgcca ctggcagcag ccactggtaa caggattagc   4380
agagcgaggt atgtaggcgg tgctacagag ttcttgaagt ggtggcctaa ctacggctac   4440
actagaagga cagtatttgg tatctgcgct ctgctgaagc cagttacctt cggaaaaaga   4500
gttggtagct cttgatccgg caaacaaacc accgctggta gcggtggttt ttttgtttgc   4560
aagcagcaga ttacgcgcag aaaaaaagga tctcaagaag atcctttgat cttttctacg   4620
gggtctgacg ctcagtggaa cgaaaactca cgttaaggga ttttggtcat gagattatca   4680
aaaaggatct tcacctagat ccttttaaat taaaaatgaa gttttaaatc aatctaaagt   4740
atatatgagt aaacttggtc tgacagttac caatgcttaa tcagtgaggc acctatctca   4800
gcgatctgtc tatttcgttc atccatagtt gcctgactcc ccgtcgtgta gataactacg   4860
atacgggagg gcttaccatc tggccccagt gctgcaatga taccgcgaga cccacgctca   4920
```

```
ccggctccag atttatcagc aataaaccag ccagccggaa gggccgagcg cagaagtggt    4980
cctgcaactt tatccgcctc catccagtct attaattgtt gccgggaagc tagagtaagt    5040
agttcgccag ttaatagttt gcgcaacgtt gttgccattg ctacaggcat cgtggtgtca    5100
cgctcgtcgt ttggtatggc ttcattcagc tccggttccc aacgatcaag gcgagttaca    5160
tgatccccca tgttgtgcaa aaaagcggtt agctccttcg gtcctccgat cgttgtcaga    5220
agtaagttgg ccgcagtgtt atcactcatg gttatggcag cactgcataa ttctcttact    5280
gtcatgccat ccgtaagatg cttttctgtg actggtgagt actcaaccaa gtcattctga    5340
gaatagtgta tgcggcgacc gagttgctct tgcccggcgt caatacggga taataccgcg    5400
ccacatagca gaactttaaa agtgctcatc attggaaaac gttcttcggg gcgaaaactc    5460
tcaaggatct taccgctgtt gagatccagt tcgatgtaac ccactcgtgc acccaactga    5520
tcttcagcat cttttacttt caccagcgtt tctgggtgag caaaaacagg aaggcaaaat    5580
gccgcaaaaa agggaataag ggcgacacgg aaatgttgaa tactcatact cttcctttt    5640
caatattatt gaagcattta tcagggttat tgtctcatga gcggatacat atttgaatgt    5700
atttagaaaa ataaacaaat aggggttccg cgcacatttc cccgaaaagt gccacctgac    5760
gtctaagaaa ccattattat catgacatta acctataaaa ataggcgtat cacgaggccc    5820
tttcgtctcg cgcgtttcgg tgatgacggt gaaaacctct gacacatgca gctcccggag    5880
acggtcacag cttgtctgta agcggatgcc gggagcagac aagcccgtca gggcgcgtca    5940
gcgggtgttg gcgggtgtcg gggctggctt aactatgcgg catcagagca gattgtactg    6000
agagtgcacc atatgcggtg tgaaataccg cacagatgcg taaggagaaa ataccgcatc    6060
aggcgccatt cgccattcag gctgcgcaac tgttgggaag ggcgatcggt gcgggcctct    6120
tcgctattac gccagctggc gaaagggggga tgtgctgcaa ggcgattaag ttgggtaacg    6180
ccagggtttt cccagtcacg acgttgtaaa acgacggcgc aaggaatggt gcatgcaagg    6240
agatggcgcc caacagtccc ccggccacgg ggcctgccac catacccacg ccgaaacaag    6300
cgctcatgag cccgaagtgg cgagcccgat cttccccatc ggtgatgtcg gcgatatagg    6360
cgccagcaac cgcacctgtg gcgccggtga tgccggccac gatgcgtccg gcgtagaggc    6420
gattagtcca atttgttaaa gacaggatat cagtggtcca ggctctagtt ttgactcaac    6480
aatatcacca gctgaagcct atagagtacg agccatagat aaaataaaag atttatttta    6540
gtctccagaa aaggggggga a                                              6561
```

<210> SEQ ID NO 12
<211> LENGTH: 6464
<212> TYPE: DNA
<213> ORGANISM: Artificial
<220> FEATURE:
<223> OTHER INFORMATION: MSCV Vector (MSCV-U6-hrGFP)

<400> SEQUENCE: 12

```
tgaaagaccc cacctgtagg tttggcaagc tagcttaagt aacgccattt tgcaaggcat     60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaatgaccc tgtgccttat ttgaactaac caatcagttc    300
gcttctcgct tctgttcgcg cgcttctgct ccccgagctc aataaaagag cccacaaccc    360
ctcactcggc gcgccagtcc tccgatagac tgcgtcgccc gggtacccgt attcccaata    420
```

```
aagcctcttg ctgtttgcat ccgaatcgtg gactcgctga tccttgggag ggtctcctca    480
gattgattga ctgcccacct cgggggtctt tcatttggag gttccaccga gatttggaga    540
cccctgccca gggaccaccg accccccgc cgggaggtaa gctggccagc ggtcgtttcg    600
tgtctgtctc tgtctttgtg cgtgtttgtg ccggcatcta atgtttgcgc ctgcgtctgt    660
actagttagc taactagctc tgtatctggc ggacccgtgg tggaactgac gagttctgaa    720
cacccggccg caaccctggg agacgtccca gggactttgg gggccgtttt tgtggcccga    780
cctgaggaag ggagtcgatg tggaatccga ccccgtcagg atatgtggtt ctggtaggag    840
acgagaacct aaaacagttc ccgcctccgt ctgaattttt gctttcggtt tggaaccgaa    900
gccgcgcgtc ttgtctgctg cagcgctgca gcatcgttct tgttgtctc tgtctgactg     960 tgtttctgta tttgtctgaa aattagggcc agactgttac cactcccta agtttgacct    1020 taggtcactg gaaagatgtc gagcggatcg ctcacaacca gtcggtagat gtcaagaaga    1080
gacgttgggt taccttctgc tctgcagaat ggccaacctt taacgtcgga tggccgcgag    1140
acggcacctt taaccgagac ctcatcaccc aggttaagat caaggtcttt tcacctggcc    1200
cgcatggaca cccagaccag gtcccctaca tcgtgacctg ggaagccttg gcttttgacc    1260
cccctccctg ggtcaagccc tttgtacacc ctaagcctcc gcctcctctt cctccatccg    1320
ccccgtctct cccccttgaa cctcctcgtt cgacccccgc tcgtatcctc cctttatcca    1380
gccctcactc cttctctagg cgccggaatt agatctttcc catgattcct tcatatttgc    1440
atatacgata caaggctgtt agagagataa ttagaattaa tttgactgta aacacaaaga    1500
tattagtaca aaatacgtga cgtagaaagt aataatttct tgggtagttt gcagtttta    1560 aaattatgtt ttaaaatgga ctatcatatg cttaccgtaa cttgaaagta tttcgatttc    1620
ttggctttat atatcttgtg gaaggacga acacctctg aggttaacgg atccgcggcc    1680
gcacgcgtct gtggaatgtg tgtcagttag ggtgtggaaa gtccccaggc tccccaggca    1740
ggcagaagta tgcaaagcat gcatctcaat tagtcagcaa ccaggtgtgg aaagtcccca    1800
ggctccccag caggcagaag tatgcaaagc atgcatctca attagtcagc aaccatagtc    1860
ccgcccctaa ctccgcccat cccgccccta actccgccca gttccgccca ttctccgccc    1920
catggctgac taatttttt tatttatgca gaggccgagg ccgcctctgc ctctgagcta    1980
ttccagaagt agtgaggagg cttttttgga ggcctaggct tttgcaaaaa gctcccggga    2040
tggtgagcaa gcagatcctg aagaacaccg gcctgcagga gatcatgagc ttcaaggtga    2100
acctggaggg cgtggtgaac aaccacgtgt tcaccatgga gggctgcggc aagggcaaca    2160
tcctgttcgg caaccagctg gtgcagatcc gcgtgaccaa gggcgccccc ctgcccttcg    2220
ccttcgacat cctgagcccc gccttccagt acggcaaccg caccttcacc aagtaccccg    2280
aggacatcag cgacttcttc atccagagct cccgccgg cttcgtgtac gagcgcaccc     2340
tgcgctacga ggacggcggc ctggtggaga tccgcagcga catcaacctg atcgaggaga    2400
tgttcgtgta ccgcgtggag tacaagggcc gcaacttccc caacgacggc ccgtgatga     2460 agaagaccat caccggcctg cagcccagct tcgaggtggt gtacatgaac gacggcgtgc    2520
tggtgggcca ggtgatcctg gtgtaccgcc tgaacagcgg caagttctac agctgccaca    2580
tgcgcaccct gatgaagagc aagggcgtgg tgaaggactt cccgagtac cacttcatcc     2640 agcaccgcct ggagaagacc tacgtggagg acggcggctt cgtggagcag cacgagaccg    2700
ccatcgccca gctgaccagc ctgggcaagc ccctgggcag cctgcacgag tgggtgtaag    2760
```

```
tcgacctgca gccaagctta tcgataaaat aaaagatttt atttagtctc cagaaaaagg   2820
ggggaatgaa agaccccacc tgtaggtttg gcaagctagc ttaagtaacg ccattttgca   2880
aggcatggaa aatacataac tgagaataga gaagttcaga tcaaggttag gaacagagag   2940
acagcagaat atgggccaaa caggatatct gtggtaagca gttcctgccc cggctcaggg   3000
ccaagaacag atggtcccca gatgcggtcc cgccctcagc agtttctaga gaaccatcag   3060
atgtttccag ggtgccccaa ggacctgaaa tgaccctgtg ccttatttga actaaccaat   3120
cagttcgctt ctcgcttctg ttcgcgcgct tctgctcccc gagctcaata aaagagccca   3180
caacccctca ctcggcgcgc cagtcctccg atagactgcg tcgcccgggt acccgtgtat   3240
ccaataaacc ctcttgcagt tgcatccgac ttgtggtctc gctgttcctt gggagggtct   3300
cctctgagtg attgactacc cgtcagcggg ggtctttcat gggtaacagt ttcttgaagt   3360
tggagaacaa cattctgagg gtaggagtcg aatattaagt aatcctgact caattagcca   3420
ctgttttgaa tccacatact ccaatactcc tgaaatagtt cattatggac agcgcagaag   3480
agctggggag aattaattcg taatcatggt catagctgtt tcctgtgtga aattgttatc   3540
cgctcacaat tccacacaac atacgagccg aagcataaa gtgtaaagcc tggggtgcct   3600
aatgagtgag ctaactcaca ttaattgcgt tgcgctcact gcccgctttc cagtcgggaa   3660
acctgtcgtg ccagctgcat taatgaatcg gccaacgcgc ggggagaggc ggtttgcgta   3720
ttgggcgctc ttccgcttcc tcgctcactg actcgctgcg ctcggtcgtt cggctgcggc   3780
gagcggtatc agctcactca aaggcggtaa tacggttatc cacagaatca ggggataacg   3840
caggaaagaa catgtgagca aaaggccagc aaaaggccag gaaccgtaaa aaggccgcgt   3900
tgctggcgtt tttccatagg ctccgccccc ctgacgagca tcacaaaaat cgacgctcaa   3960
gtcagaggtg gcgaaacccg acaggactat aaagatacca ggcgtttccc cctggaagct   4020
ccctcgtgcg ctctcctgtt ccgaccctgc cgcttaccgg atacctgtcc gcctttctcc   4080
cttcgggaag cgtggcgctt tctcatagct cacgctgtag gtatctcagt tcggtgtagg   4140
tcgttcgctc caagctgggc tgtgtgcacg aaccccccgt tcagcccgac cgctgcgcct   4200
tatccggtaa ctatcgtctt gagtccaacc cggtaagaca cgacttatcg ccactggcag   4260
cagccactgg taacaggatt agcagagcga ggtatgtagg cggtgctaca gagttcttga   4320
agtggtggcc taactacggc tacactagaa ggacagtatt tggtatctgc gctctgctga   4380
agccagttac cttcggaaaa agagttggta gctcttgatc cggcaaacaa accaccgctg   4440
gtagcggtgg tttttttgtt tgcaagcagc agattacgcg cagaaaaaaa ggatctcaag   4500
aagatccttt gatcttttct acggggtctg acgctcagtg gaacgaaaac tcacgttaag   4560
ggattttggt catgagatta tcaaaaagga tcttcaccta gatcctttta aattaaaaat   4620
gaagttttaa atcaatctaa agtatatatg agtaaacttg gtctgacagt taccaatgct   4680
taatcagtga ggcacctatc tcagcgatct gtctatttcg ttcatccata gttgcctgac   4740
tccccgtcgt gtagataact acgatacggg agggcttacc atctggcccc agtgctgcaa   4800
tgataccgcg agacccacgc tcaccggctc cagatttatc agcaataaac cagccagccg   4860
gaagggccga gcgcagaagt ggtcctgcaa ctttatccgc ctccatccag tctattaatt   4920
gttgccggga agctagagta agtagttcgc cagttaatag tttgcgcaac gttgttgcca   4980
ttgctacagg catcgtggtg tcacgctcgt cgtttggtat ggcttcattc agctccggtt   5040
cccaacgatc aaggcgagtt acatgatccc ccatgttgtg caaaaaagcg gttagctcct   5100
tcggtcctcc gatcgttgtc agaagtaagt tggccgcagt gttatcactc atggttatgg   5160
```

```
cagcactgca taattctctt actgtcatgc catccgtaag atgcttttct gtgactggtg    5220
agtactcaac caagtcattc tgagaatagt gtatgcggcg accgagttgc tcttgcccgg    5280
cgtcaatacg ggataatacc gcgccacata gcagaacttt aaaagtgctc atcattggaa    5340
aacgttcttc ggggcgaaaa ctctcaagga tcttaccgct gttgagatcc agttcgatgt    5400
aacccactcg tgcacccaac tgatcttcag catcttttac tttcaccagc gtttctgggt    5460
gagcaaaaac aggaaggcaa aatgccgcaa aaaagggaat aagggcgaca cggaaatgtt    5520
gaatactcat actcttcctt tttcaatatt attgaagcat ttatcagggt tattgtctca    5580
tgagcggata catatttgaa tgtatttaga aaaataaaca atagggggtt ccgcgcacat    5640
ttccccgaaa agtgccacct gacgtctaag aaaccattat tatcatgaca ttaacctata    5700
aaaataggcg tatcacgagg ccctttcgtc tcgcgcgttt cggtgatgac ggtgaaaacc    5760
tctgacacat gcagctcccg gagacggtca cagcttgtct gtaagcggat gccgggagca    5820
gacaagcccg tcagggcgcg tcagcgggtg ttggcgggtg tcggggctgg cttaactatg    5880
cggcatcaga gcagattgta ctgagagtgc accatatgcg gtgtgaaata ccgcacagat    5940
gcgtaaggag aaaataccgc atcaggcgcc attcgccatt caggctgcgc aactgttggg    6000
aagggcgatc ggtgcgggcc tcttcgctat tacgccagct ggcgaaaggg ggatgtgctg    6060
caaggcgatt aagttgggta acgccagggt tttcccagtc acgacgttgt aaaacgacgg    6120
cgcaaggaat ggtgcatgca aggagatggc gcccaacagt cccccggcca cggggcctgc    6180
caccataccc acgccgaaac aagcgctcat gagcccgaag tggcgagccc gatcttcccc    6240
atcggtgatg tcggcgatat aggcgccagc aaccgcacct gtggcgccgg tgatgccggc    6300
cacgatgcgt ccggcgtaga ggcgattagt ccaatttgtt aaagacagga tatcagtggt    6360
ccaggctcta gttttgactc aacaatatca ccagctgaag cctatagagt acgagccata    6420
gataaaataa aagatttat ttagtctcca gaaaagggg ggaa                      6464
```

```
<210> SEQ ID NO 13
<211> LENGTH: 62
<212> TYPE: DNA
<213> ORGANISM: Artificial
<220> FEATURE:
<223> OTHER INFORMATION: p38 target gene insert

<400> SEQUENCE: 13
ccggtgcagg agttgaacaa gacaatacct gattgtcttg ttcagctcct gcttttttgga    60 ag                                                                   62

<210> SEQ ID NO 14
<211> LENGTH: 100
<212> TYPE: DNA
<213> ORGANISM: Artificial
<220> FEATURE:
<223> OTHER INFORMATION: H1 promoter sequence

<400> SEQUENCE: 14
ccctttctca ccagagtatg tcttgaatat tctaagggtt taggtttctg taaagtgcaa    60
ataccactaa agggtcttgt gtatcgctgt acgtttataa                         100
```